US008114348B2

(12) United States Patent
Caracci et al.

(10) Patent No.: US 8,114,348 B2
(45) Date of Patent: Feb. 14, 2012

(54) LABEL-FREE HIGH THROUGHPUT BIOMOLECULAR SCREENING SYSTEM AND METHOD

(75) Inventors: Stephen J. Caracci, Elmira, NY (US); Volker H. O. Eckelt, Jena (DE); Anthony G. Frutos, Painted Post, NY (US); Mark F. Krol, Painted Post, NY (US); Thomas C. Moore, Jena (DE); David A. Pastel, Horseheads, NY (US); Gordon M. Shedd, Lawrenceville, PA (US)

(73) Assignee: Corning Incorporated, Corning, NY (US)

( * ) Notice: Subject to any disclaimer, the term of this patent is extended or adjusted under 35 U.S.C. 154(b) by 127 days.

(21) Appl. No.: 12/480,886

(22) Filed: Jun. 9, 2009

(65) Prior Publication Data

US 2009/0247427 A1      Oct. 1, 2009

Related U.S. Application Data

(63) Continuation of application No. 11/489,173, filed on Jul. 19, 2006, now abandoned.

(60) Provisional application No. 60/701,445, filed on Jul. 20, 2005.

(51) Int. Cl.
*G01N 21/00* (2006.01)
*G01N 35/00* (2006.01)
*G01N 21/75* (2006.01)

(52) U.S. Cl. ............... 422/63; 422/64; 422/65; 422/400; 422/401; 422/402; 422/403; 422/404; 435/286.2; 435/287.2

(58) Field of Classification Search .................. None
See application file for complete search history.

(56) References Cited

U.S. PATENT DOCUMENTS

| 4,815,843 A | 3/1989 | Tiefenthaler et al. ......... 356/128 |
| 4,952,056 A | 8/1990 | Tiefenthaler ................. 356/73.1 |
| 4,971,514 A | 11/1990 | Hunter |

(Continued)

FOREIGN PATENT DOCUMENTS

DE        20101080        6/2002

(Continued)

OTHER PUBLICATIONS

A.J. Pope et al., "Homogeneous fluorescence readouts for miniaturized high-throughput screening: theory and practice", Drug Discovery Today, vol. 4, No. 8, Aug. 1999, pp. 350-362.

(Continued)

*Primary Examiner* — Jill Warden
*Assistant Examiner* — Neil N Turk
(74) *Attorney, Agent, or Firm* — Gregory B. Butler; Timothy M. Schaeberle

(57) ABSTRACT

A screening system and method are described herein which provide a unique and practical solution for enabling label-free high throughput screening (HTS) to aid in the discovery of new drugs. In one embodiment, the screening system enables direct binding assays to be performed in which a biomolecular interaction of a chemical compound (drug candidate) with a biomolecule (therapeutic target) can be detected using assay volumes and concentrations that are compatible with the current practices of HTS in the pharmaceutical industry. The screening system also enables the detection of bio-chemical interactions that occur in the wells of a microplate which incorporates biosensors and surface chemistry to immobilize the therapeutic target at the surface of the biosensors. The screening system also includes fluid handling and plate handling devices to help perform automated HTS assays.

14 Claims, 16 Drawing Sheets

U.S. PATENT DOCUMENTS

| | | | |
|---|---|---|---|
| 5,262,842 A | 11/1993 | Gauglitz et al. | 356/345 |
| 5,313,264 A | 5/1994 | Ivarsson et al. | 356/73 |
| 5,459,300 A | 10/1995 | Kasman | 219/433 |
| 5,470,744 A | 11/1995 | Astle | 435/286.7 |
| 5,738,825 A | 4/1998 | Rudigier et al. | 422/82.11 |
| 6,018,388 A | 1/2000 | Nawracala et al. | 356/246 |
| 6,129,428 A | 10/2000 | Helwig et al. | 312/114 |
| 6,200,814 B1 | 3/2001 | Malmqvist et al. | 436/52 |
| 6,395,558 B1 | 5/2002 | Duveneck et al. | 436/172 |
| 6,455,004 B1 | 9/2002 | Tiefenthaler | 422/91 |
| 6,478,524 B1 | 11/2002 | Malin | 414/283 |
| 6,710,877 B2 | 3/2004 | Chase et al. | 356/432 |
| 6,721,053 B1 | 4/2004 | Maseeh | 356/436 |
| 6,767,607 B2 | 7/2004 | Tanner et al. | 428/131 |
| 6,785,433 B2 | 8/2004 | Tiefenthaler | 385/12 |
| 6,787,110 B2 | 9/2004 | Tiefenthaler | 422/91 |
| 6,818,886 B2 | 11/2004 | Tiefenthaler | 250/282 |
| 6,829,073 B1 | 12/2004 | Krol et al. | 359/263 |
| 6,958,131 B2 | 10/2005 | Tiefenthaler | 422/82.05 |
| 6,985,664 B2 | 1/2006 | Caracci et al. | 385/130 |
| 7,057,720 B2 | 6/2006 | Caracci et al. | 356/300 |
| 7,136,550 B2 | 11/2006 | Mozdy | 385/28 |
| 2001/0048899 A1 | 12/2001 | Marouiss et al. | |
| 2001/0055817 A1 | 12/2001 | Malmqvist et al. | 436/531 |
| 2002/0009391 A1 | 1/2002 | Marquiss et al. | 422/63 |
| 2002/0037237 A1 | 3/2002 | Mainquist et al. | |
| 2002/0090320 A1 | 7/2002 | Burow et al. | 422/64 |
| 2002/0127565 A1 | 9/2002 | Cunningham et al. | 435/6 |
| 2002/0168295 A1 | 11/2002 | Cunningham et al. | 422/82.05 |
| 2003/0003018 A1 | 1/2003 | Stolowitz et al. | 422/82.05 |
| 2003/0017083 A1 | 1/2003 | Pobering et al. | |
| 2003/0017580 A1 | 1/2003 | Cunningham et al. | 435/287.2 |
| 2003/0017581 A1 | 1/2003 | Li et al. | 435/287.2 |
| 2003/0026891 A1 | 2/2003 | Qiu et al. | 427/58 |
| 2003/0027327 A1 | 2/2003 | Cunningham et al. | 435/287.2 |
| 2003/0027328 A1 | 2/2003 | Cunningham et al. | 435/287.2 |
| 2003/0031829 A1 | 2/2003 | Tanner et al. | 428/131 |
| 2003/0032039 A1 | 2/2003 | Cunningham et al. | 435/6 |
| 2003/0059855 A1 | 3/2003 | Cunningham et al. | 435/7.9 |
| 2003/0068657 A1 | 4/2003 | Lin et al. | 435/7.9 |
| 2003/0077660 A1 | 4/2003 | Pien et al. | 435/7.1 |
| 2003/0092075 A1 | 5/2003 | Pepper | 435/7.9 |
| 2003/0113766 A1 | 6/2003 | Pepper et al. | 435/6 |
| 2003/0205511 A1 | 11/2003 | Olivier et al. | |
| 2004/0132172 A1 | 7/2004 | Cunningham et al. | 435/287.2 |
| 2004/0132214 A1 | 7/2004 | Lin et al. | 436/518 |
| 2004/0151626 A1 | 8/2004 | Cunningham et al. | 422/58 |
| 2004/0191765 A1 | 9/2004 | Mozdy et al. | 435/5 |
| 2004/0223881 A1 | 11/2004 | Cunningham et al. | 422/82.05 |
| 2004/0239922 A1 | 12/2004 | Modlin et al. | |
| 2004/0247486 A1 | 12/2004 | Tiefenthaler | 422/82.11 |
| 2005/0070027 A1 | 3/2005 | Gollier et al. | 436/518 |
| 2005/0099622 A1 | 5/2005 | Caracci et al. | 356/300 |
| 2005/0136534 A1 | 6/2005 | Austin et al. | |
| 2005/0170498 A1 | 8/2005 | Dolley et al. | 435/288.4 |
| 2005/0236554 A1 | 10/2005 | Fontaine et al. | 250/208.1 |
| 2005/0264818 A1 | 12/2005 | Gollier | 356/445 |
| 2005/0272046 A1* | 12/2005 | Schermer et al. | 435/6 |
| 2006/0062509 A1 | 3/2006 | Krol et al. | 385/12 |
| 2006/0106557 A1 | 5/2006 | Fontaine et al. | 702/87 |
| 2006/0110594 A1 | 5/2006 | Frutos et al. | 428/332 |
| 2006/0139641 A1 | 6/2006 | Gollier et al. | 356/399 |
| 2006/0141527 A1 | 6/2006 | Caracci et al. | 435/7.1 |
| 2006/0141611 A1 | 6/2006 | Frutos et al. | 435/287.2 |
| 2006/0146317 A1 | 7/2006 | Aklian | 356/128 |
| 2006/0180750 A1 | 8/2006 | Gollier et al. | 250/227.11 |
| 2006/0182382 A1 | 8/2006 | Gollier et al. | 385/12 |
| 2006/0223051 A1 | 10/2006 | Fang et al. | 435/4 |
| 2006/0229818 A1 | 10/2006 | Fang et al. | 702/19 |
| 2007/0020152 A1 | 1/2007 | Costello, III et al. | |

FOREIGN PATENT DOCUMENTS

| | | |
|---|---|---|
| EP | 0 570 445 | 8/1996 |
| EP | 0 660 924 | 9/1999 |
| EP | 1358937 | 11/2003 |
| JP | 2004-239777 | 8/2004 |
| JP | 2004-529324 | 9/2004 |
| WO | WO 90/05295 | 5/1990 |
| WO | WO 95/22754 | 8/1995 |
| WO | 9621855 | 7/1996 |
| WO | WO 98/09156 | 3/1998 |
| WO | WO 99/09392 | 2/1999 |
| WO | 0196880 | 12/2001 |
| WO | 02/061429 | 8/2002 |
| WO | WO 02/079761 | 10/2002 |
| WO | 2005031349 | 4/2005 |

OTHER PUBLICATIONS

M.A. Sills et al., "Comparison of Assay Technologies for a Tyrosine Kinase Assay Generates Different Results in HTS", Journal of Biomolecular Screening, vol. 7, 2002, pp. 191-.

J. Comley, "Label-Free Detection—New Biosensors Facilitate Broader Range of Drug Discovery Application", Drug Discovery World, Winter 2004, vol. 5, pp. 63-74.

M.A. Cooper, "Current biosensor technologies in drug discovery", Drug Discovery World Summer 2006, pp. 68-82.

J. Comley, "New Options for Cell-Based Assay Automation", Drug Discovery World Fal 2005, pp. 39-62.

C. Eggeling et al., "Highly sensitive fluorescence detection technology currently available for HTS", DDT, vol. 8, No. 14, Jul. 2003, pp. 632-641.

J.R. Denmark et al., "Standardization of enzyme-linked immunosorbent assay (ELISA) and the detection of Toxoplasma antibody", Medical Laboratory Science, 1978, vol. 35, pp. 227-232.

"Working Group Updates", Journal of Biomolecular Screening, vol. 1, No. 4, 1996, pp. 163-168.

Cunningham, B., et al., "A plastic colorimetric resonant optical biosensor for multiparallel detection of label-free biochemical interactions", Sensors and Actuators B, vol. 85, No. 3, Jul. 25, 2002, pp. 219-226.

Frutos, Anthony G., "A New Label-Free Detection Platform for High Throughput Screening", Conference Info: Proceedings Labautomation 2005, Jan. 31, 2005, Abstract.

* cited by examiner

LABEL-FREE HIGH THROUGHPUT BIOMOLECULAR SCREENING SYSTEM AND METHOD

CROSS REFERENCE TO RELATED APPLICATION

This Application is a continuation application of U.S. patent application Ser. No. 11/489,173, filed Jul. 19, 2006, now abandoned, which claims priority to U.S. Patent Application No. 60/701,445, filed Jul. 20, 2005. The contents of these two documents are incorporated by reference herein.

BACKGROUND OF THE INVENTION

1. Field of the Invention

The present invention relates to a high throughput biomolecular screening system and method that use a label independent optical detection technique to interrogate biosensors which are incorporated within the wells of a microplate. In the preferred embodiment, the high throughput biomolecular screening system includes automated instruments for dispensing, mixing, incubating, microplate handling, and implementing measurement protocols to provide high throughput detection and analysis of biomolecular interactions that take place on the biosensors in the microplate.

2. Description of Related Art

Today many areas of biological research utilize label free detection technologies to help perform sensitive and time-constrained assays. A typical assay involves the detection of a chemical/biochemical compound (drug candidate) binding to an immobilized molecule (the therapeutic target) at the surface of individual optical sensors (biosensors) located at the bottom of each well in a disposable microplate. And, the potential for using label free detection technologies to perform high throughput screening (HTS) assays in the drug discovery process was recently discussed in the following article:

John Comley "LABEL-FREE DETECTION-New Biosensors Facilitate Broader Range of Drug Discovery Applications'", Drug Discovery World, Winter 2004/5, pages 63-74.

In this article, one of the systems described utilizes a label free detection technology based on Surface Plasmon Resonance (SPR). For instance, U.S. Pat. No. 5,313,264 assigned to Pharmacia Biosensor AB discloses an analytical system that uses SPR and microfluidics to detect biomolecular interactions in real time on four sensing areas. In addition, U.S. Patent Application No. 2003/0003018A1 assigned to Prolinx Incorporated discloses instruments and systems that use miniaturized SPR sensors to enable the real time analysis of molecular interactions. Because, both of these systems are designed for real time kinetic analysis of molecular interactions, they have limited multiplexing capabilities which limits their throughput such that they cannot be used in HTS. Furthermore, these systems do not use standardized SBS 96, 384 or 1536 microplates. The first drawback is also true for screening systems based on non-optical detection principles (Cf. John Comley's article). Accordingly, there is a need to provide a label-free technology that enables the label free detection of a bio-chemical interaction between a drug compound and a biomolecule in high throughput primary screens. This need and other needs are satisfied by the high throughput biomolecular screening system and method of the present invention.

BRIEF DESCRIPTION OF THE INVENTION

The present invention includes a screening system and method which provide a unique and practical solution for enabling label-free high throughput screening (HTS) to aid in the discovery of new drugs. In one embodiment, the screening system enables direct binding assays to be performed in which a biomolecular interaction of a chemical compound (drug candidate) with a biomolecule (therapeutic target) can be detected using assay volumes and concentrations that are compatible with the current practices of HTS in the pharmaceutical industry. The screening system also enables the detection of bio-chemical interactions that occur in the wells of a microplate which incorporates biosensors and surface chemistry to immobilize the therapeutic target at the surface of the biosensors. The screening system also includes fluid handling and plate handling devices to help perform automated HTS assays.

BRIEF DESCRIPTION OF THE DRAWINGS

A more complete understanding of the present invention may be had by reference to the following detailed description when taken in conjunction with the accompanying drawings wherein.

DETAILED DESCRIPTION OF THE DRAWINGS

Figure 1A:
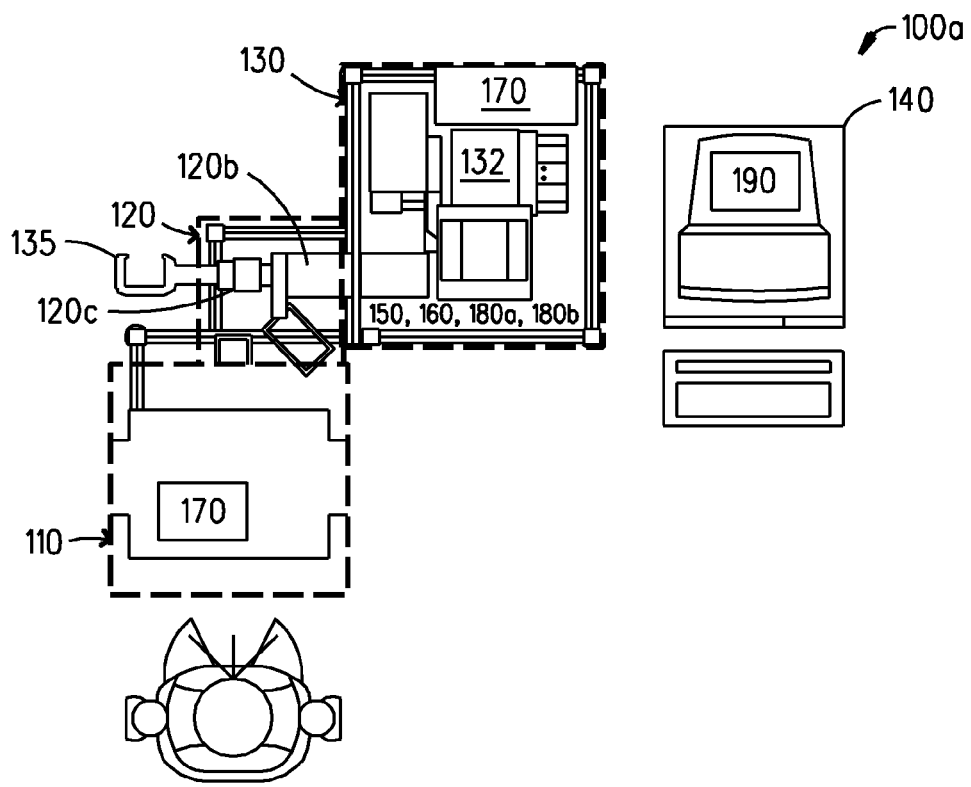
FIGS. 1A-1C are block diagrams that show the basic components of several different screening systems in accordance with the present invention.
Figure 1B:
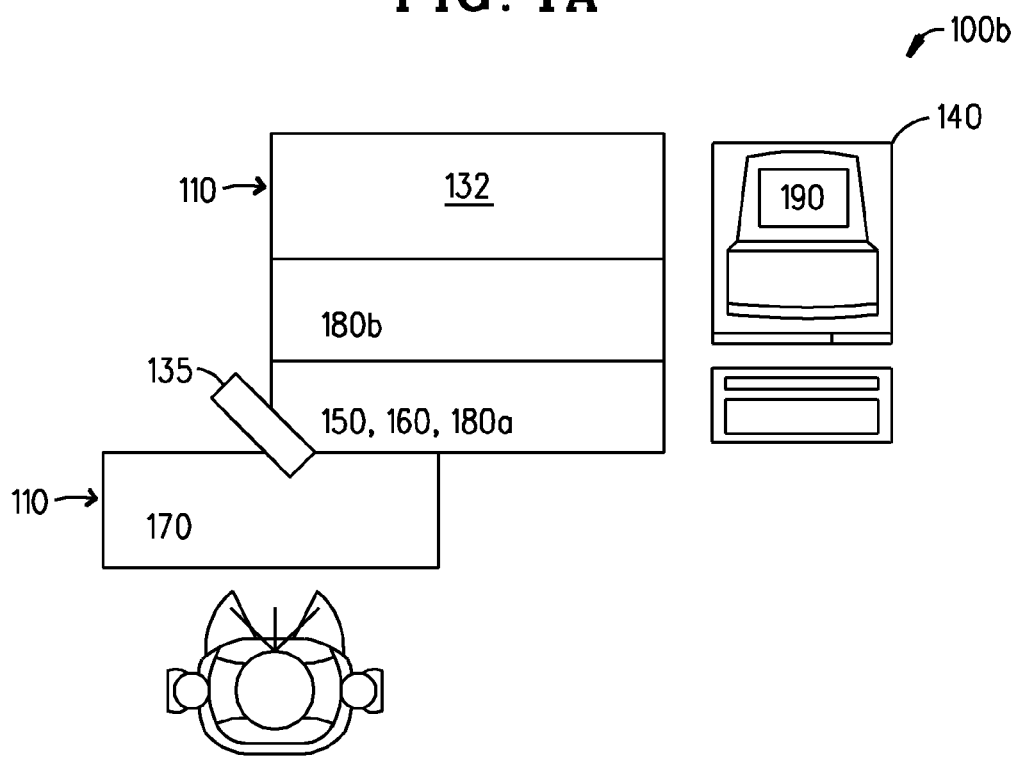
Figure 1C:
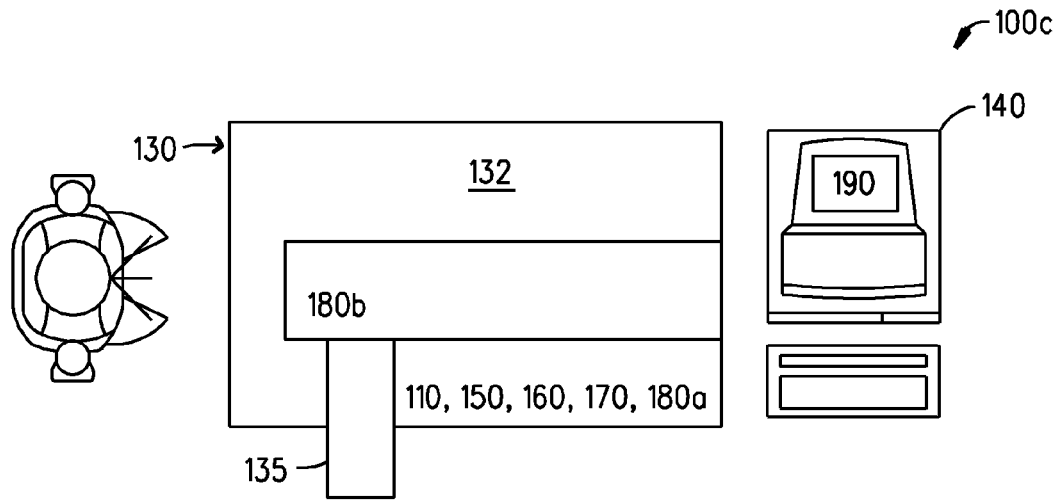

Referring to FIGS. 1A-1C, there are three block diagrams of three screening systems 100a, 100b and 100c each of which can along with one or more disposable microplates be used to perform high throughput screenings of drug compound libraries using a label-free optical detection technology. Basically, the screening systems 100a, 100b and 100c generate assay data relative to the binding of a chemical/biochemical compound (drug candidate) to an immobilized molecule (the therapeutic target) at the surface of individual optical sensors (biosensors) located at the bottom of each well in the disposable microplates.

The screening systems 100a, 100b and 100c all have slightly different configurations but as will be discussed below they all have the same capabilities and can perform high throughput screenings of drug compound libraries in disposable microplates using a label-free optical detection technology. As shown in FIG. 1A, the screening system 100a includes an incubation chamber 110 (athermalization buffer 110), a load lock chamber 120, a measurement chamber 130, an interface device 135, and a computer 140. In this embodiment, the athermalization buffer 110 operates to receive, store and maintain a predetermined temperature around one or more microplates. The load lock chamber 120 has an area in which a microplate is moved while travelling from the athermalization buffer 110 to the measurement chamber 130 and vice versa. The measurement chamber 130 maintains a predetermined temperature around a microplate and also has a measurement nest 132 that is used to position/reposition the microplate to a high degree of accuracy before the biosensors that are incorporated within the wells of the microplate are optically interrogated. And, the interface device 135 is used to move microplates between the load lock chamber 130 and external equipment (e.g., see FIG. 13).

As shown in FIG. 1B, the screening system 100b includes an incubation chamber 110 (athermalization buffer 110), a measurement chamber 130, an interface device 135, and a computer 140. The screening system 100b has the same configuration as screening system 100a except that there is no load lock chamber 120 and the interface device 135 can be used to move microplates from the athermalization buffer 110 to the measurement chamber 130. In contrast, the screening system 100c shown in FIG. 1C includes a measurement chamber 130, an interface device 135, and a computer 140. This screening system 100c has the same configuration as screening system 100b except that the athermalization buffer 110 is located within the measurement chamber 130. In all of the different screening systems 100a, 100b and 100c, the computer 140 enables a large number of different label-free assays to be performed by controlling the various components and subsystems within the screening systems 100a, 100b and 100c. Some of these subsystems are as follows:

1.1 Optical subsystem 150.
1.2 Plate alignment subsystem 160.
1.3 Environmental control subsystem 170.
1.4 Fluid handling and plate transport subsystems 180a and 180b.
1.5 Computer/Software subsystem 190.

Figure 13:
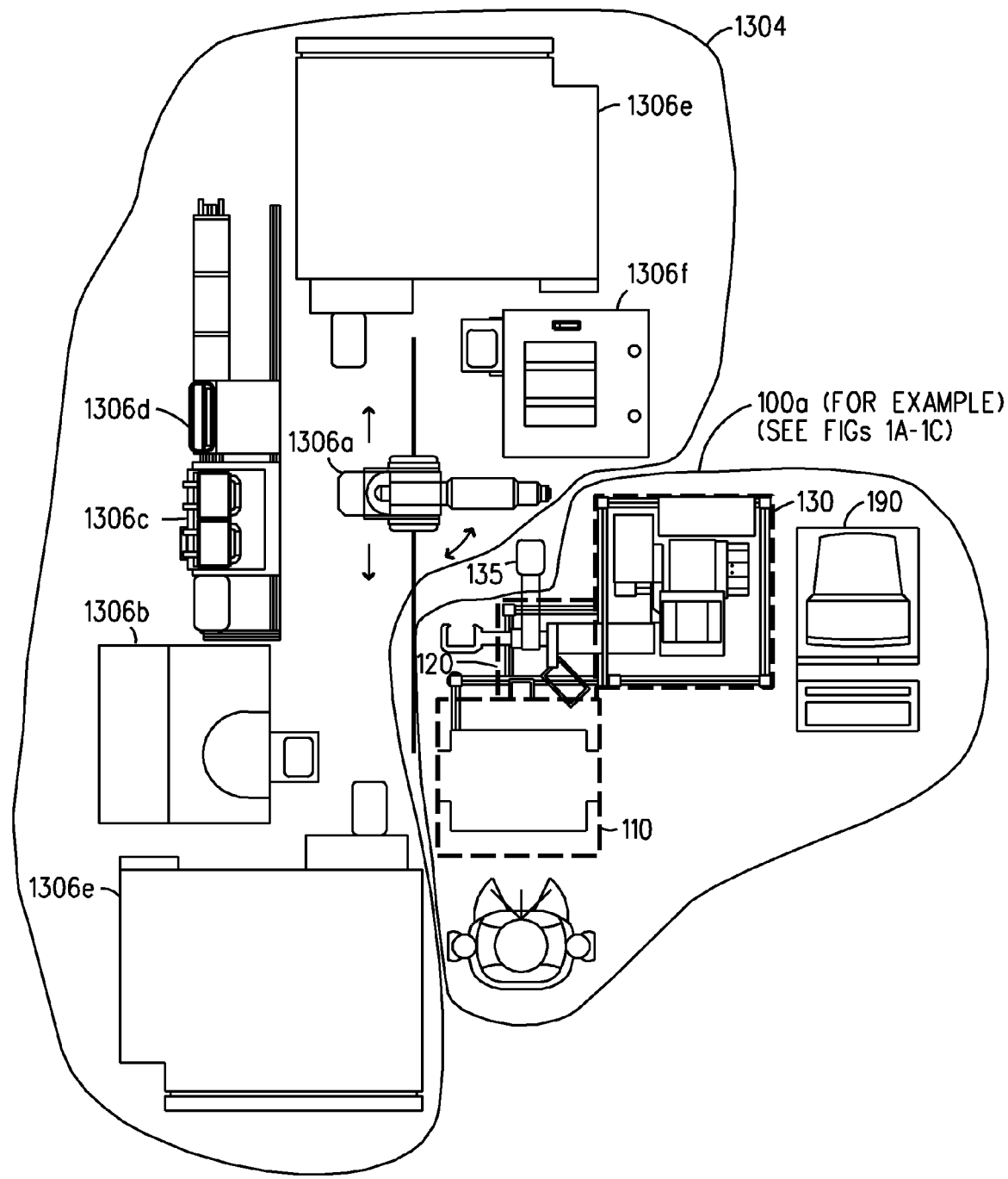

1.6 Device 135 which interfaces screening system 100 and external equipment 1304 (see FIG. 13).

1.1 Optical Subsystem 150

Figure 2:
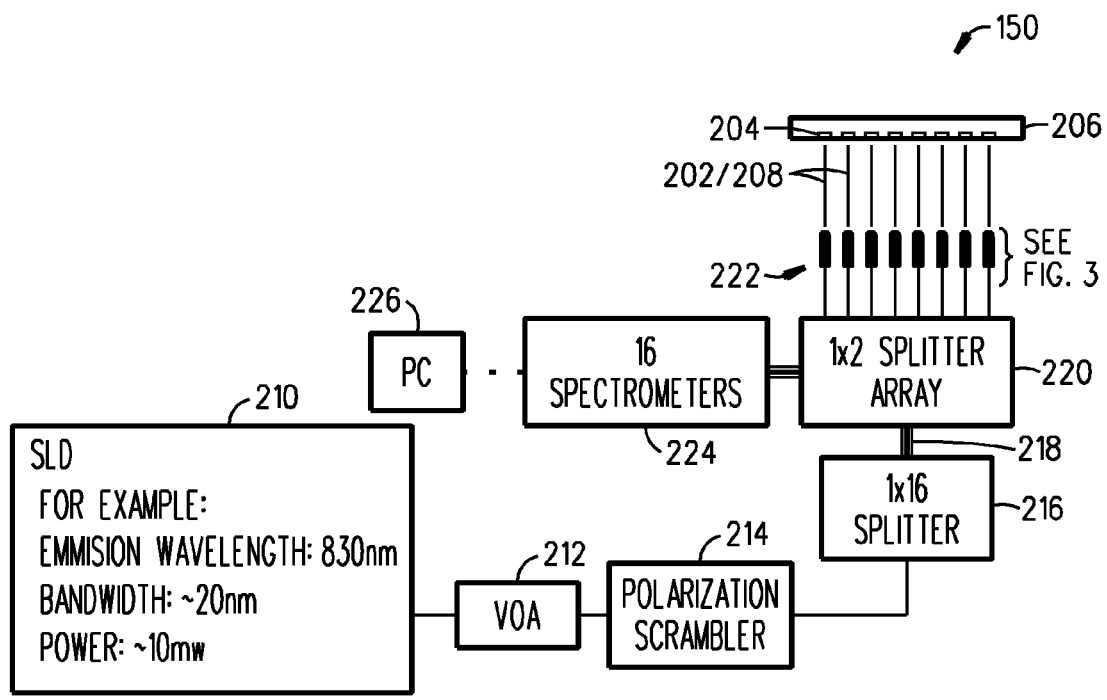
FIGS. 2 and 3 are diagrams that illustrate the basic components of a preferred optical subsystem that can be used in any one of the screening systems shown in FIGS. 1A-1C in accordance with the present invention.
Figure 3:
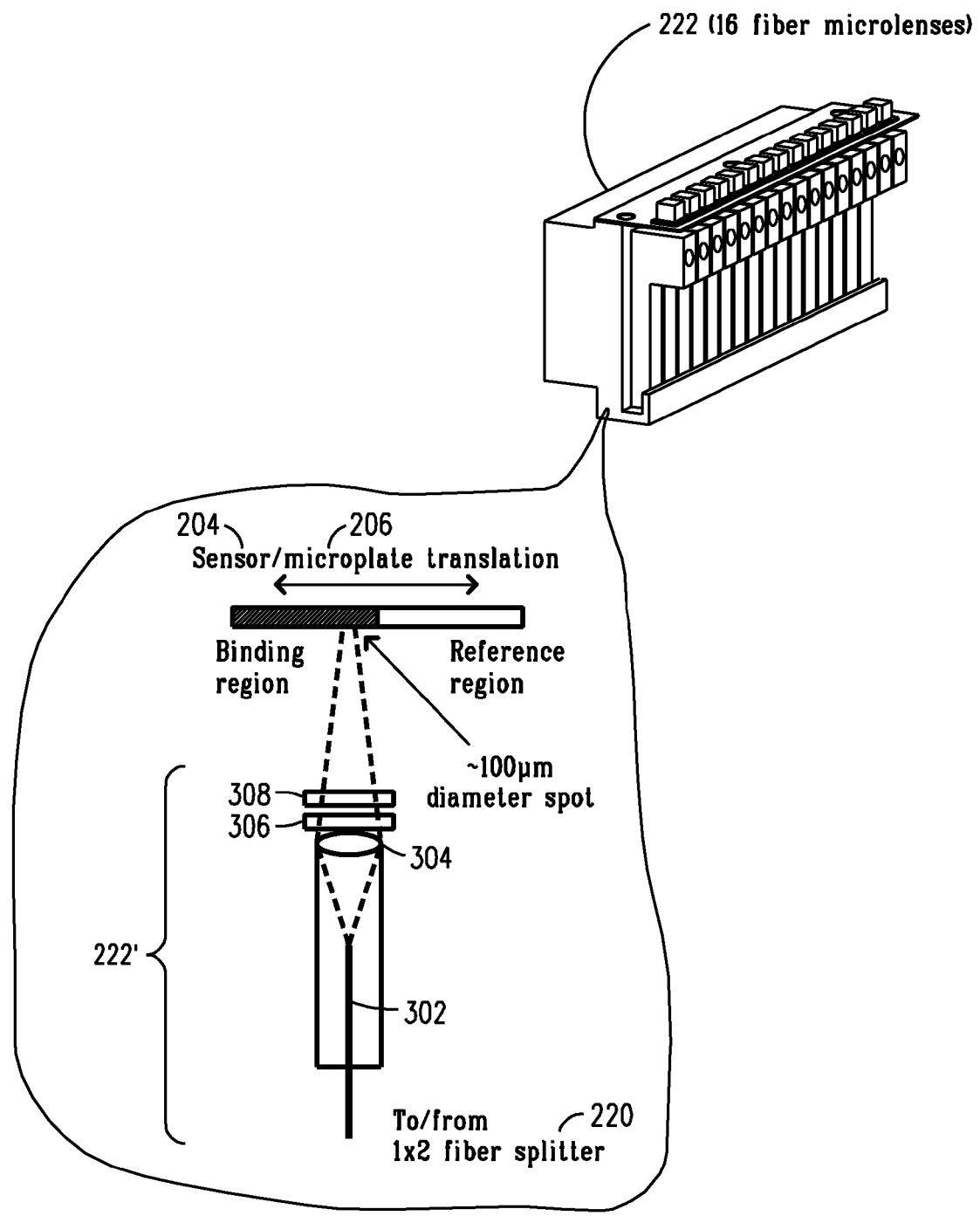

FIGS. 2 and 3 are diagrams that illustrate the different components in one embodiment of the optical subsystem 150. Basically, the optical subsystem 150 operates to deliver light beams 202 to the optical sensors 204 (shown located in a microplate 206) and also operates to collect the reflected light beams 208. The optical system 150 is located within the measurement chamber 130 (see FIGS. 1A-1C).

In one embodiment, the optical subsystem 150 has a light source 210 (superluminescent diode (SLD) 210) which is fiberized and connected to a variable optical attenuator (VOA) 212 that is connected to a polarization scrambler 214. The polarization scrambler 214 outputs a light beam which is split by a 1×16 splitter 216 into 16 individual optical fibers 218. A 1×2 splitter array 220 having 16 channels connects each optical fiber 216 to one of 16 fiber pigtailed microlenses 222 (optical head 222) (see FIG. 3). Each fiber pigtailed microlens 222 delivers a light beam 202 to a moving biosensor 204 (or static biosensor 204) and also receives a reflected light beam 208. Typically, the reflected light beam 208 has a narrow band of wavelengths with a width around 1-2 nm. The reflected light beam 208 passes through the 1×2 splitter array 220 and is detected by one of 16 spectrometers 224. The spectrometer 224 is used to measure the peak of the reflected light beam 208. The spectral data associated with this peak of the reflected light beam 208 is then processed by a personal computer (PC) 226. The personal computer 226 (which can be computer 140) determines the resonance wavelength which corresponds to the centroid (or squared centroid) of the peak of the reflected light beam 208. Alternatively, the PC 226 can calculate the center wavelength by using for example an autocorrelation method or a maximum derivative method.

The resonance wavelength indicates whether or not the chemical/biochemical compound (drug candidate) interacted with an immobilized molecule (the therapeutic target) on the surface of one of the biosensors 204 located at the bottom of each well in the disposable microplate 206. This biochemical interaction like material binding, adsorption etc. . . . alters the refractive index on top of the biosensor 204 which alters the biosensor's optical response and hence the measured wavelength and makes it possible to directly monitor biological events in label-free assays. It should be noted that an increase of the refractive index as sensed by the biosensors 204 produce an increase in the wavelength of the reflected light 208.

Referring to FIG. 3, it can be seen that each fiber pigtailed microlens 222 includes a single mode fiber 302, a lens 304, a linear polarizer 306 and a λ/4 plate 308. Alternatively, a circular polarizer can be used instead of the linear polarizer 306 and the λ/4 plate 308. This particular fiber pigtailed microlens 222 has an angular acceptance of about 5 milliradians and a spot diameter on the biosensor 204 of around 100 μm. And, this particular fiber pigtailed microlens 222 is configured to reject problematical Fresnel reflections from the microplate 206. However, problematical parasitic reflections which are generated by multiple reflections in the substrate 706 can pass the circular polarizer (linear polarizer 306 and λ/4 plate 308). But, these parasitic reflections can be removed by either digital filtering of the signal, or alignment adjustments of the spectrometers 224. The 16 fiber pigtailed microlenses 222 can be adjusted along 5 axis (pitch, roll, X, Y and theta). In one embodiment, the microplate 206 is moved in one direction (1-D scan) such that multiple biosensors 204 and multiple regions within each individual biosensor 204 can be interrogated. For a detailed discussion about this type of optical subsystem 150 reference is made to the following documents:

U.S. patent application Ser. No. 11/027,547 entitled "Spatially Scanned Optical Reader System and Method for Using Same".

U.S. patent application Ser. No. 10/977,520 entitled "Single-Fiber Launch/Receive System for Biosensing Applications".

U.S. patent application Ser. No. 10/856,572 entitled "Optical Interrogation Systems With Reduced Parasitic Reflections and a Method for Filtering Parasitic Reflections".

U.S. patent application Ser. No. 11/058,155 entitled "Single Mode (SM) Fiber Optical Reader System and Method for Interrogating Resonant Waveguide-Grating Sensor(s)".

The contents of these documents are incorporated by reference herein.

In addition, the following documents describe other types of optical subsystems 150 that could be implemented in the present invention:

U.S. patent application Ser. No. 10/602,304 entitled "Optical Interrogation System and Method for Using Same".

U.S. patent application Ser. No. 11/019,439 entitled "Arrayed Sensor Measurement System and Method"

U.S. Pat. No. 6,785,433 entitled "Waveguide Grid Array and Optical Measurement Arrangement".

U.S. patent application Ser. No. 11/100,199 entitled "Optical Interrogation System and Method for 2-D Sensor Arrays".

The contents of these documents are incorporated by reference herein.

1.2 Plate Alignment Subsystem 160.

Figure 4A:
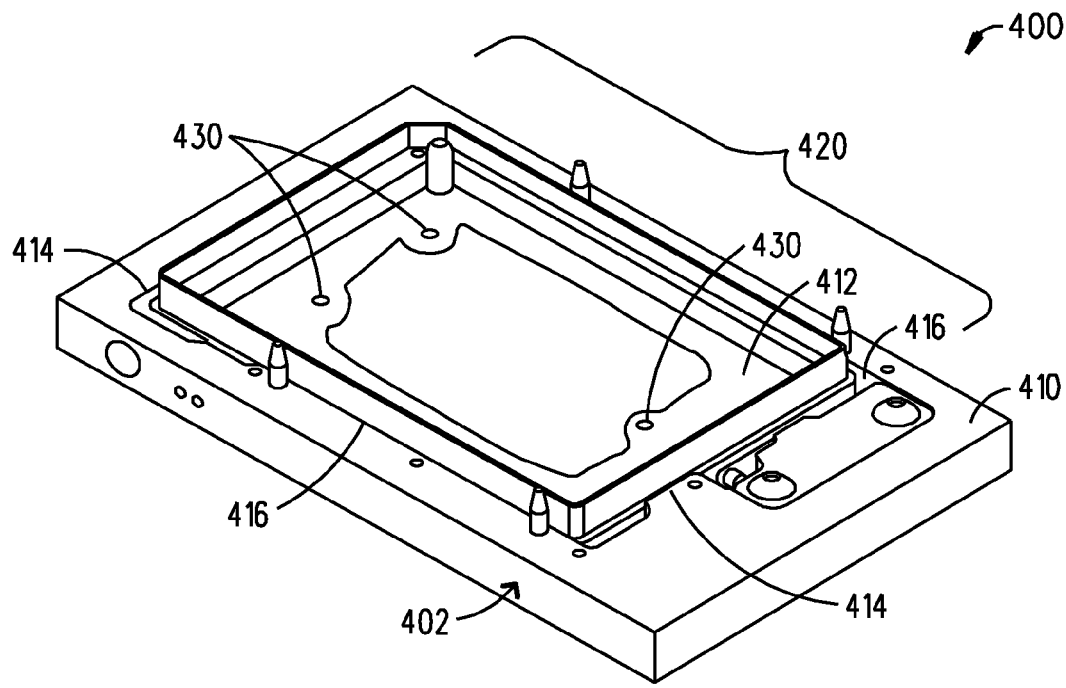
FIGS. 4A and 4B are diagrams that illustrate the basic components of a preferred microplate alignment subsystem that can be used in any one of the screening systems shown in FIGS. 1A-1C in accordance with the present invention.
Figure 4B:
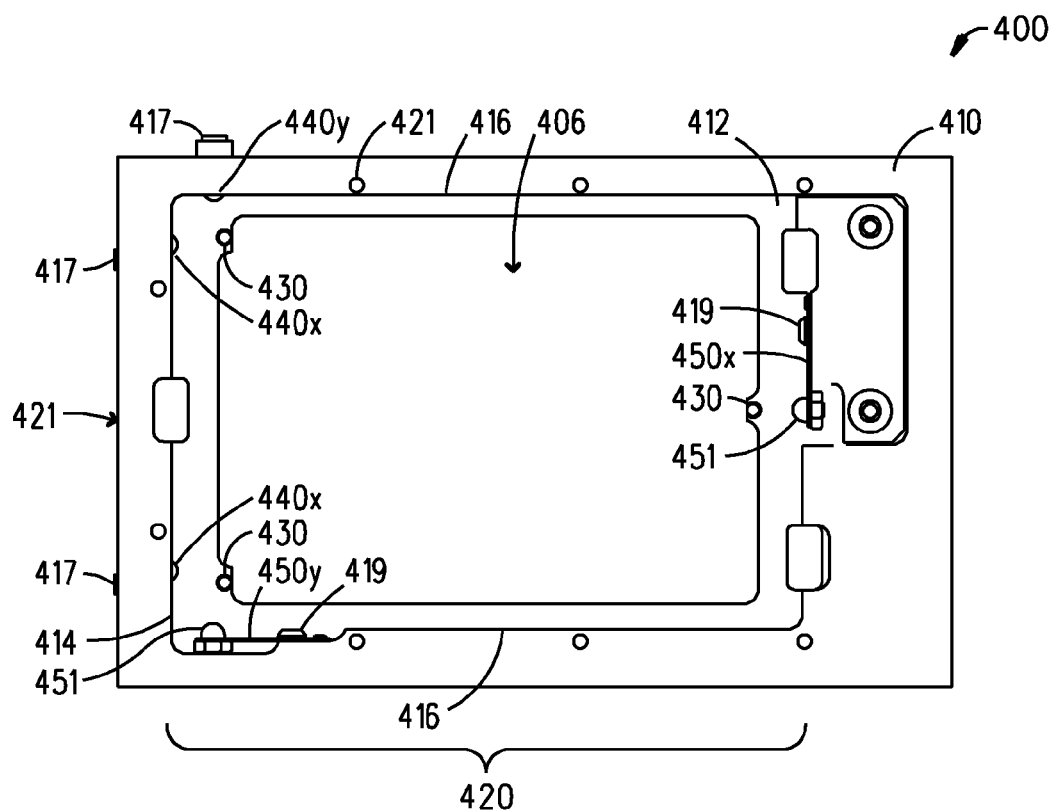

FIGS. 4A and 4B are diagrams that illustrate the different components in one embodiment of the plate alignment subsystem 160. Basically, the plate alignment subsystem 160 includes an X/Y translation stage (not shown) and a microplate mounting mechanism 400 that coordinates and moves the microplate 206 so it can be properly scanned by the optical subsystem 150. The plate alignment subsystem 160 is located within the measurement chamber 130 (see FIG. 1).

In one embodiment, the plate alignment subsystem 160 has a microplate mounting mechanism 400 which comprises a base 402 with two surfaces, one primary surface 410 and a secondary surface 412. The secondary surface 412 is inset on the end walls 414 and side walls 416 that form the opening/detection aperture 406 within the base 402. The secondary surface 412 forms a ledge, peripheral to the detection aperture 406, and defines a nesting receptacle 420. The nesting receptacle 420 forms the area to be occupied by a secured microplate 206 (see FIGS. 6A and 6B). The nesting receptacle 420 is further defined by the secondary surface 412 which has three supports 430 that are capable of supporting and contacting a microplate 206 in the Z-directional plane. It is preferable, however, for the restraint mechanism 400 to have eight contact points to establish the position of a microplate 206 in the X, Y, and Z planar directions as seen in a top view of the preferred restraint mechanism 400 in FIG. 4B. The eight contact points in this restraint mechanism 400 include: three supports 430 within the nesting receptacle 420 positioned in a triangular configuration and projecting from the surface 412, as well as five additional positioning structures, two contacts in the X-direction 440x located on an end wall 414, one contact in the Y-direction 440y located on a side wall 416, and two spring-loaded contacts 450x and 450y located on an opposite end wall 414 and a side wall 416, respectively.

Adjustments 417 for each of these positioning contacts 440x/y are located on an exterior surface 421 of the restraint mechanism 400. Leaf-spring adjustments 419 are utilized to adjust applicable spring forces. Such adjustments 417 or leaf-spring adjustments 419 may be screws or alternative means for adjusting the forces applied to a microplate 206. Additional adjustments may be utilized to accommodate alternative microplate dimensions (i.e. adjustments for the heights of the supports 430). For a more detailed discussion about this particular restraint mechanism 400 and other restraint mechanisms reference is made to the following document:

U.S. Patent Application Ser. No. 60/701,452 entitled "Kinematic Wellplate Mounting Method".

The contents of this document are incorporated by reference herein.

1.3 Environmental Control Subsystem 170.

The environmental control subsystem 170 is used to minimize the influence of the external environment (e.g. temperature fluctuations) within the incubation chamber 110, the load lock chamber 120 and the measurement chamber 130 of the screening system 100 (see FIG. 1). In one embodiment, the environmental control subsystem 170 includes an enclosure with thermoelectric modules and air circulation device which allows one to control the temperature within 50 millidegrees (3 sigma, 12 hours). The environmental control subsystem 170 is shown in this example located within the measurement chamber 130 (see FIG. 1).

1.4 Fluid Handling and Plate Transport Subsystems 180a and 180b.

The fluid handling and plate transport subsystems 180a and 180b are used to move one or more microplates 206 within the measurement chamber system 110. In one embodiment, the fluid handling subsystem 180a has a pipettor (not shown) that can transfer fluids between the assay microplate 206 and the source microplate (not shown). And, the plate transport subsystem 180b has a gripper (not shown) which is used to move one microplate 206 (assay microplate) into a measurement position and to move another microplate (source microplate) into a fluid handling position. In the preferred embodiment, the plate transport subsystem 180b operates to move microplates into and out of the measurement position. It can include one or more of the following components such as rotating arms, plate carriages, grippers, lifters and conveyor systems (for example). Basically, the plate transport subsystem 180b provides a means for enabling multiple microplates to be in the measurement chamber 130. For example, when one microplate is being measured (optically interrogated), another microplate can be moved into position to be measured next, and the previous microplate can be moved out of the screening system 100. A more detailed description about these subsystems 180a and 180b is provided below with respect to FIGS. 11-15.

1.5 Computer 140/Software Subsystem 190.

Figure 5:
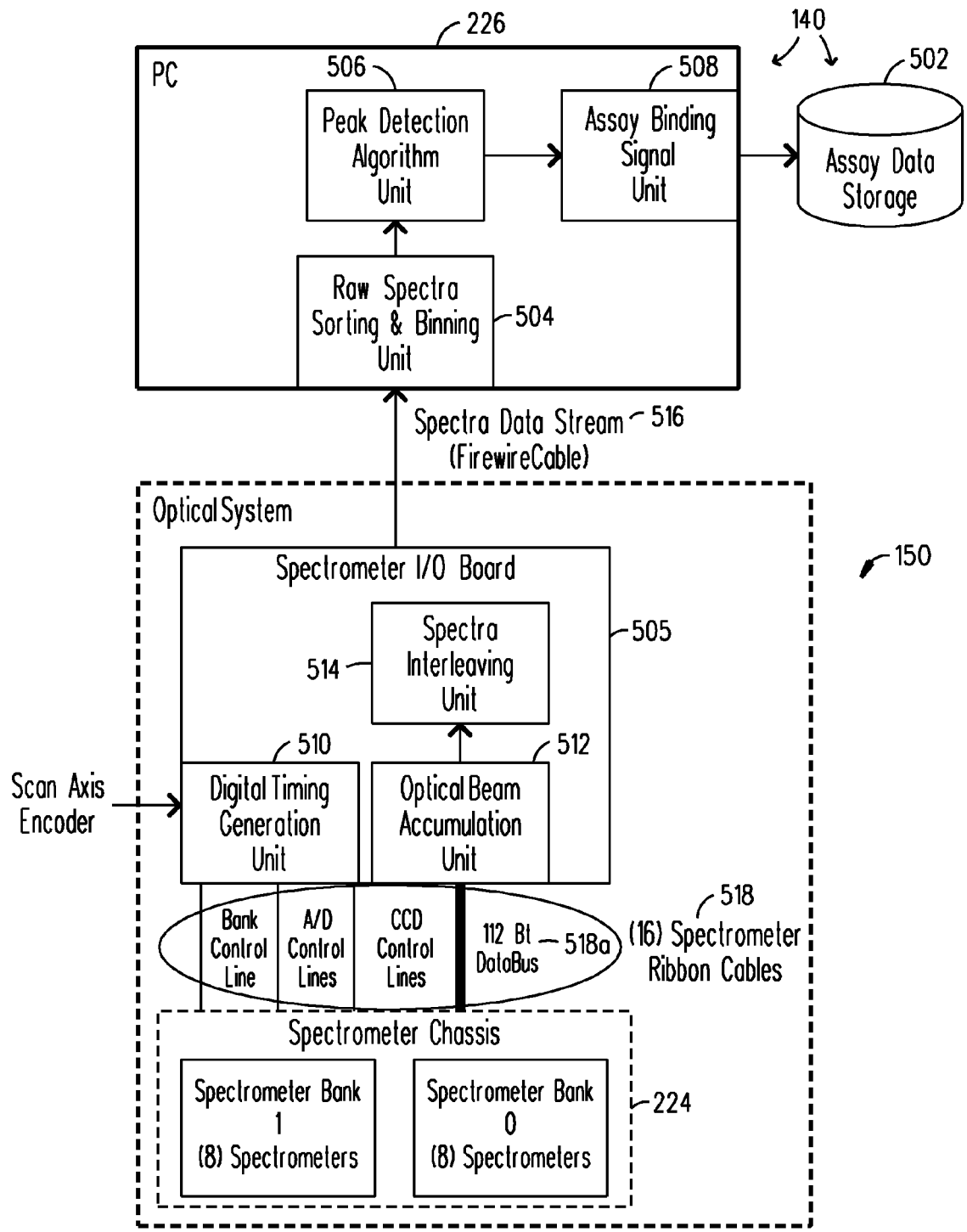
FIG. 5 is a diagram that illustrates the basic components of a preferred computer/software subsystem that can be used in any one of the screening systems shown in FIGS. 1A-1C in accordance with the present invention.

The computer 140/software subsystem 190 controls the instrument hardware in the screening system 100 and also coordinates the measurement and processes the data obtained from the interrogation of the microplate 206. An exemplary electrical architecture of the computer 140/software subsystem 190 and the optical subsystem 150 is depicted in FIG. 5. In this example, the computer/software subsystem 190 includes a PC 226 (see FIG. 2) and a data storage unit 502. The PC 226 has the following components: (1) raw spectra sorting and binning unit 504; (2) peak detection algorithm unit 506; and (3) assay binding signal unit 508 (which is connected to the data storage unit 502). And, the PC 226 is coupled to the optical subsystem 150 via a spectra data stream 516. The optical subsystem 150 (see FIG. 2) includes a spectrometer I/O board 505 and spectrometers 224. The spectrometer I/O board 505 has the following components: (1) digital timing generation unit 510; (2) optical beam accumulation unit 512; and (3) spectra interleaving unit 514. And, the spectrometer I/O board 505 is coupled to the spectrometers 224 via ribbon cables 518. Each of these components perform/function as follows:

1.5.1 Digital Timing Generation Unit 510

The spectrometer IO board 505 provides and keeps track of all the real time digital signals for the optics module 150. To help it do this, the digital timing generation unit 510 receives a quadrature encoder input from a scanning axis encoder that is associated with the translation stage and restraining mechanism 400 which moves and supports the microplate 206 (see FIGS. 4A and 4B). Based on the velocity of the translation stage, the digital timing generation unit 510 coordinates the precisely timed acquisition of spectra by the spectrometers 224. In the preferred embodiment, all 16 spectrometers 224 simultaneously sample regions of their respective biosensors 204. The digital timing generation 510 also has a number of control lines in the ribbon cable 518 which are used to drive both a CCD array and an A/D converter in each of the spectrometers 224. The CCD arrays convert the optical signals into analog electrical signals which represent the power at each given pixel (wavelength). And, the A/D converters convert the analog signals into digital signals. These digital signals are presented to the spectrometer IO board 505 via the 112 Bit data bus 518a.

1.5.2 112 Bit Data Bus 518a

Each A/D converter in each spectrometer 224 presents a 14 bit signal to the spectrometer IO board 505. For each clocked pixel, there is a 14 bit number that represents the signal level on that pixel. The 14 bit buses from each of 8 spectrometers in one of the two banks are ganged together to create a 112 bit data bus 518a. Each spectrometer ribbon cable contains 14 bits of A/D data. At the spectrometer IO board 505, the 112 bit data bus 518a is connected to a 112 bit FPGA input port (not shown). Both banks of 8 spectrometers 224 share the same 112 bit data bus 518a. In addition, the digital timing generation unit 510 uses a bank control line to control which bank of spectrometers 224 is allowed to use the 112 bit data bus 518a. Only one bank of 8 spectrometers 224 can write to the 112 data bus 518 at any given time.

1.5.3 Optical Beam Accumulation Unit 512

As the raw spectra is being accumulated from the spectrometers 224, the spectrometer IO board 505 is able to either pass the raw spectra up to the PC 226, or, it is able to perform gain and offset calibrations to the pixel data and then accumulate a series of raw spectra to effectively create a larger "virtual" optical beam 208.

1.5.4 Spectra Interleaving Unit 514

Based on how the spectra are collected and optionally accumulated, it may be necessary to interleave the pixel data from each spectrometer 224 together before sending the data to the PC 226. So, for example, pixel#1 of spectrometer #1, and then pixel #1 of spectrometer#2 may need to be interleaved before being sent to the PC 226.

1.5.5 Spectra Data Stream 516

The spectra that is collected by the spectrometer IO board 505 can be uploaded to the PC 226 over a 32 MB/sec firewire channel 516. In this case, the host PC 226 would have a firewire card that directs the data into internal memory (not shown).

1.5.6. Raw Spectra Sorting and Binning Unit 504

Based on how the data was collected, the spectra may need to be sorted back into spectral waveforms for each optical channel. Also, further accumulation similar to what was done on the spectrometer IO board 505 could take place at this time to create a larger "virtual" optical beam 208.

1.5.7 Peak Detection Algorithm Unit 506

Each raw spectra, or series of raw spectra that are accumulated together are then processed with a peak detection algorithm that attempts to resolve the position of the resonance on the CCD array in each of the spectrometers 224.

1.5.8 Assay Binding Signal Unit 508

The assay binding signal unit 508 uses the output from the peak detection algorithm unit 506 to calculate the assay binding signal based on the type of microplate 206 that was inserted into the measurement chamber 130. For example, a well 610 that is using self referencing would take the signal pad wavelength minus the reference pad wavelength as the binding signal (see FIG. 6A). And, a well 610 that doesn't use referencing would simply use the average wavelength for the entire well as an unreferenced binding signal.

The PC 226 also has a graphic user interface (not shown) at which an operator can chose between an assay development mode in which the reflected light peak positions of a given row of sensors are monitored in real time or a high throughput screening mode in which the microplate is fully scanned and individual data are generated for each well. Both of these modes are described in detail below with respect to FIGS. 11-15.

1.6 Device 135

This device 135 functions as an interface with external equipment like a high throughput screening (HTS) line 1304 which is shown in FIG. 13. The device 135 can include, but is not limited to: a rotating arm, a drawer, a lifter, a gripper, a carriage on rails, or a conveyor belt. Its main function is to move microplate 206 in and out of the screening system 100. It can also send microplates to either the incubator chamber 110 or the measurement chamber 130.

Figure 6A:
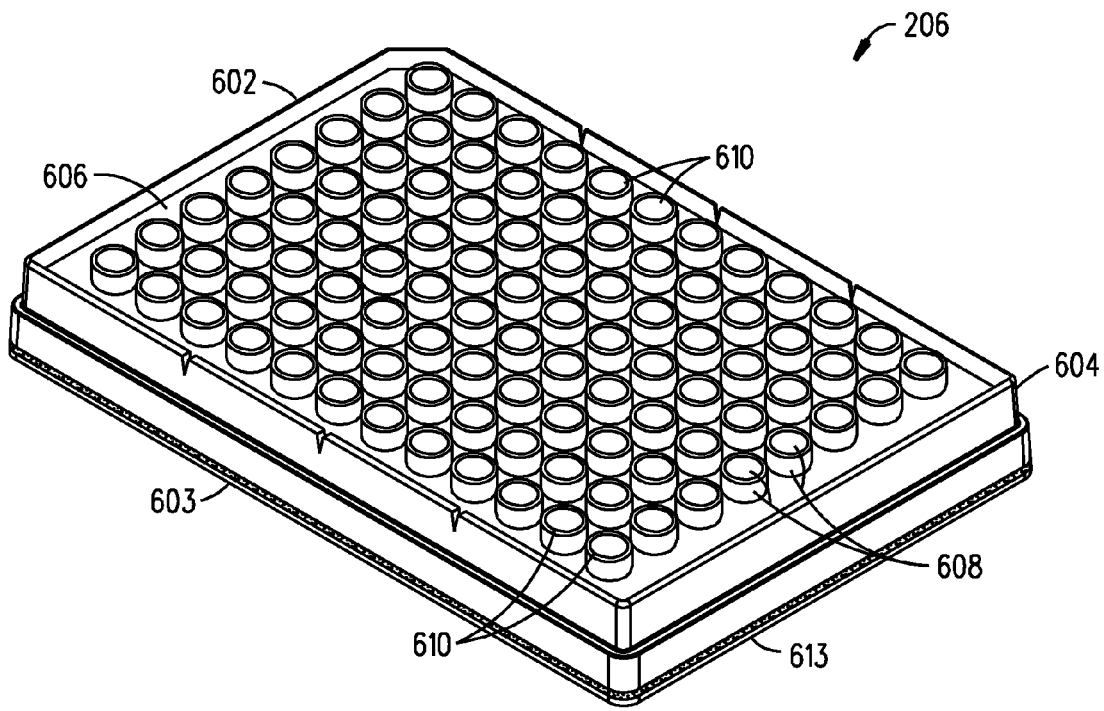
FIGS. 6A-6B are two diagrams of an exemplary microplate (e.g., multiwell plate) which can be interrogated by anyone of the screening systems shown in FIGS. 1A-1C in accordance with the present invention.
Figure 6B:
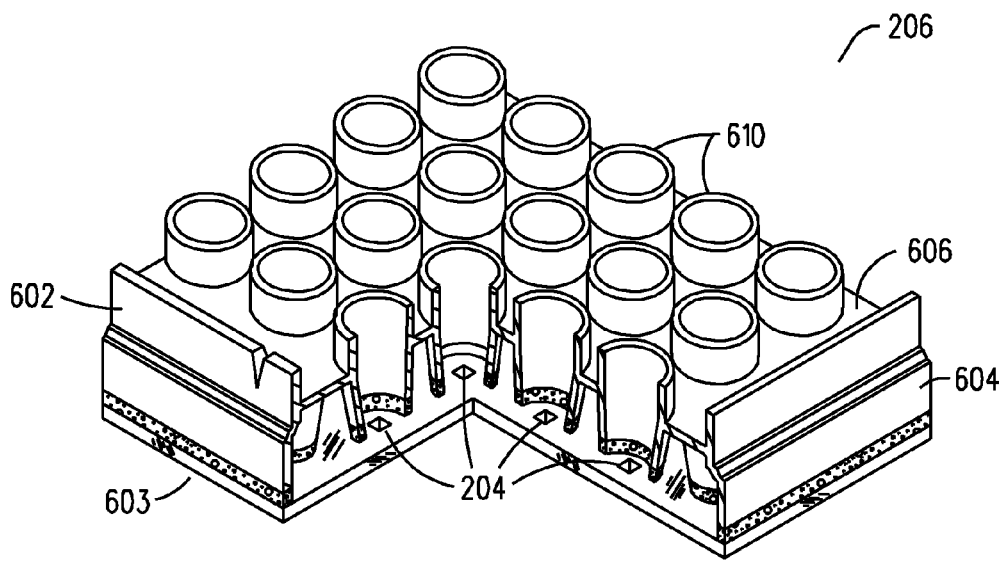

A description is provided next about an exemplary disposable microplate 206 that can be interrogated by the screening system 100. FIGS. 6A and 6B are two diagrams which illustrate an exemplary disposable microplate 206 (e.g., multiwell plate) capable of being positioned in the restraining mechanism 400 (see FIGS. 4A and 4B). The microplate 206 shown has an array of wells 610 and a two-part construction including an upper plate 602 and a lower plate 603. The upper plate 602 includes a peripheral skirt/frame 604, a top surface 606, and sidewalls 608 to delineate the wells 610. Each well 610 is capable of receiving an aliquot of sample to be assayed. The lower plate 603 forms a substantially and preferably flat transparent bottom wall/surface 613 for each well 610 in which a biosensor 204 is formed or located (see FIG. 6B). The biosensor 204 is used to detect biomolecular activity occurring within the well 610 or, alternatively, on the bottom surface of the well 610. Although, the microplate 206 shown has 96 wells 610 it should be appreciated that in the preferred embodiment a 384 well microplate 206 is utilized. Following is a detailed description about some of the components in the microplate 206 which are as follows:

2.1 Biosensor 204.
  2.2 Biosensor's base plate 603.
  2.3 Upper (holey) plate 602/base plate 603 assembly.
  2.4 Biosensor's surface attachment chemistry.
  2.5 Biosensor's signal/reference areas.

2.1 Biosensor 204.

Figure 7:
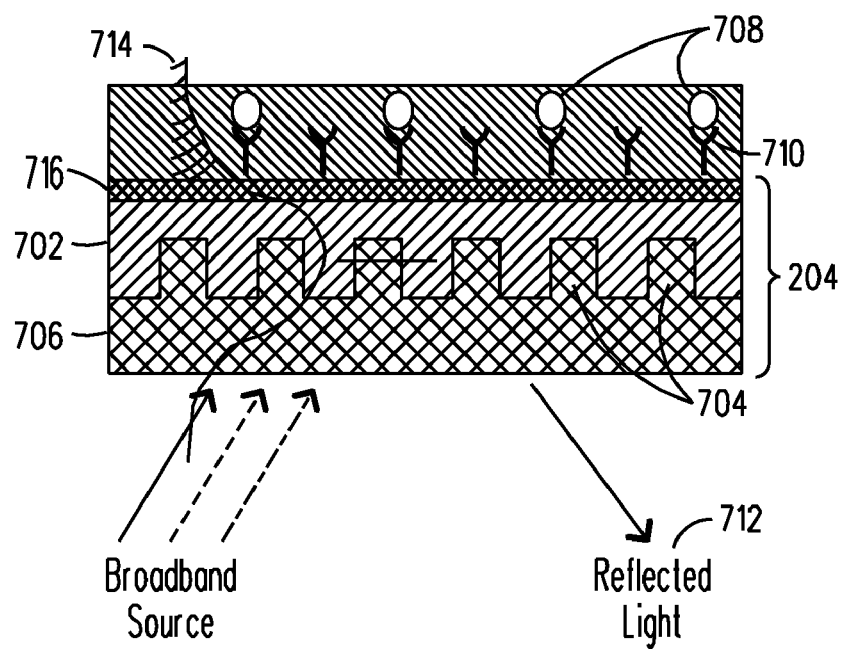
FIG. 7 is a diagram which illustrates the basic components of a biosensor (e.g., resonant waveguide grating (RWG) biosensor) which can be incorporated within a well of the microplate shown in FIGS. 6A-6B.

In one embodiment, the biosensor 204 is a resonant waveguide grating (RWG) biosensor 204 which has a structure as shown in FIG. 7. The biosensor 204 comprises a high refractive index waveguide 702 that is deposited on a replicated diffraction grating 704 which is laid down on a glass substrate 706. For example, the diffraction grating 704 can be a 3 mm×3 mm square which has a replicated linear grating with a pitch of 500 nm, a depth of 50 nm and a 50% duty cycle. Preferably, the thickness and refractive index of the waveguide 702 along with the characteristics (pitch, depth, and duty cycle) of the diffraction grating 704 are optimized to yield the highest sensitivity to a refractive index change which is caused by the interaction of the analyte 708 and target 710 on top of the biosensor 204. This sensitivity is defined as the shift of the reflected light 712 relative to the refractive index change (nm/refractive index unit). Because, the sensing principle involves the interaction of an evanescent wave 714 emerging from the biosensor 204, the sensed volume is typically limited to the first 150-200 nm above the surface of the waveguide 702.

For a more detailed discussion about the structure and functionality of the biosensor 204, reference is made to the following documents:
- U.S. Pat. No. 4,815,843 entitled "Optical Sensor for Selective Detection of Substances and/or for the Detection of Refractive Index Changes in Gaseous, Liquid, Solid and Porous Samples".
- U.S. Pat. No. 5,738,825 entitled "Optical Biosensor Matrix".

The contents of these documents are incorporated by reference herein.

Figure 8A:
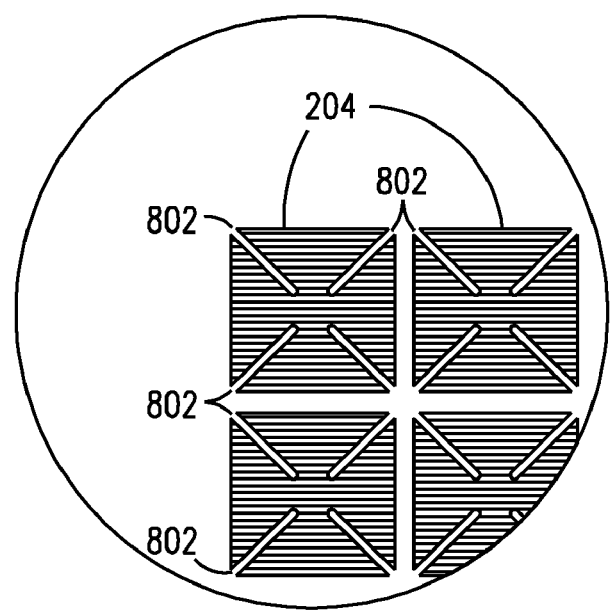
FIG. 8A is a diagram which illustrates an alternative design for a biosensor which has fiducials that can be incorporated within a well of the microplate shown in FIGS. 6A-6B.
Figure 8B:
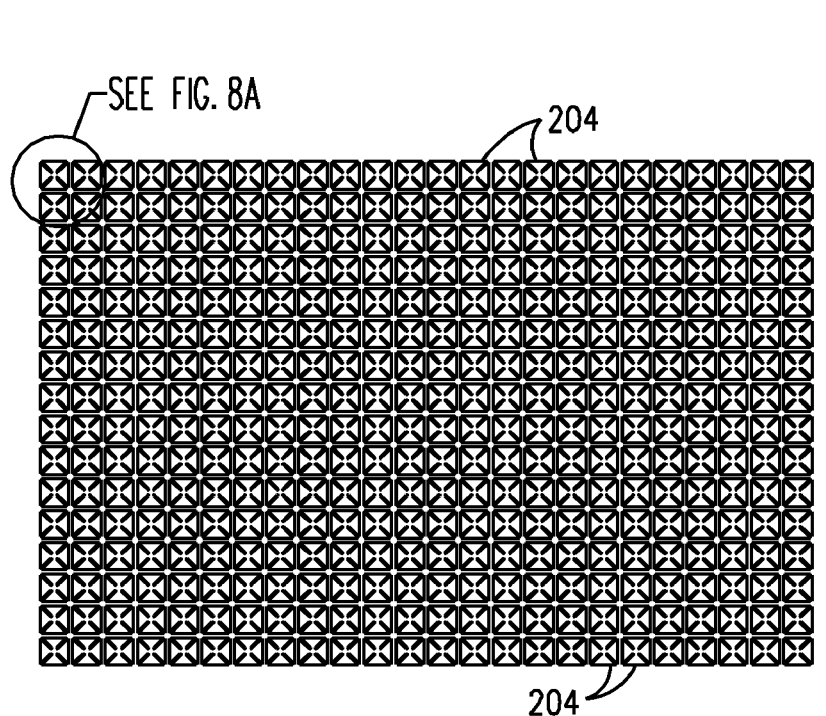
FIG. 8B is a top view of a base plate in a microplate that has 384 biosensors incorporated therein that are configured like the biosensor shown in FIG. 8A.
Figure 9A:
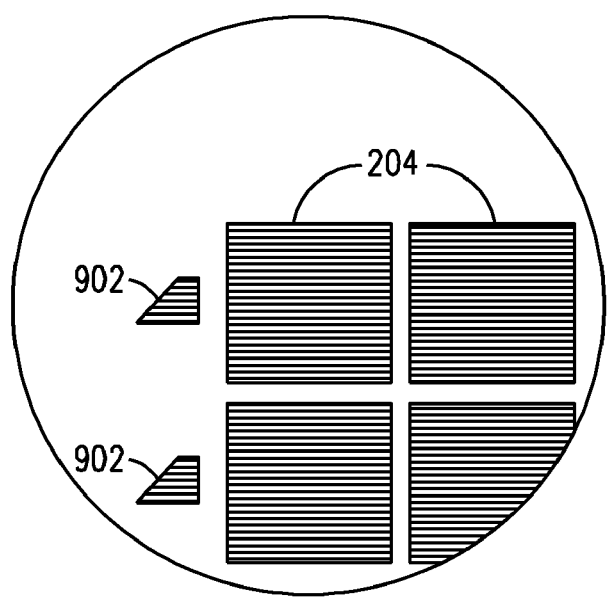
FIGS. 9A-9B are two diagrams which illustrate an alternative design for a microplate in which the biosensors do not have fiducials but the microplate has the fiducials formed therein.
Figure 9B:
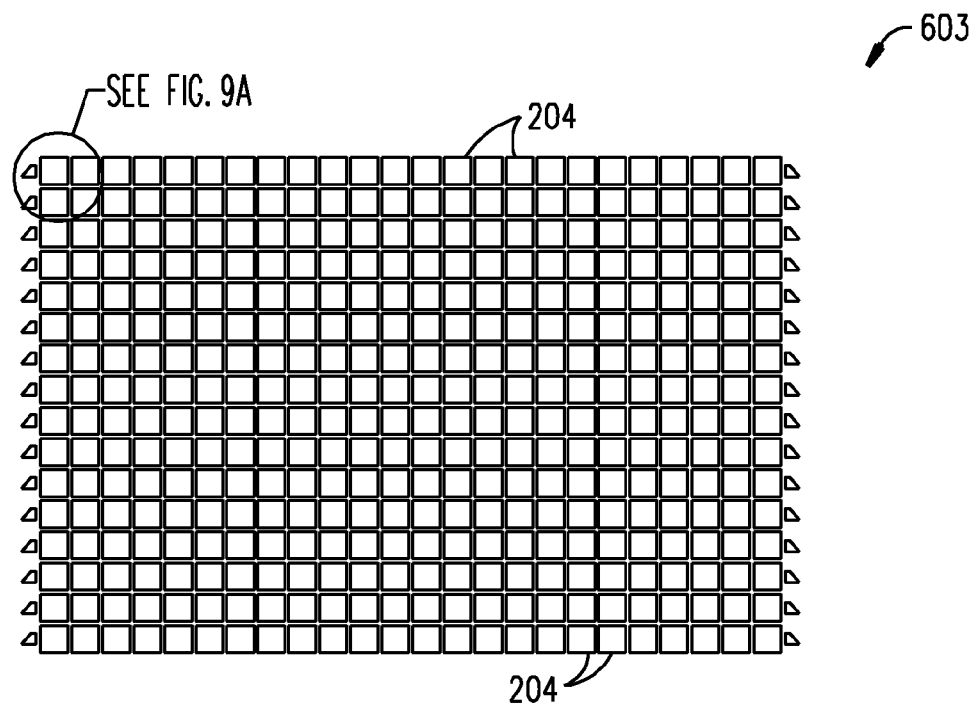

FIGS. 8A and 8B are diagrams illustrating an alternative design for the biosensor 204 which has fiducials 802 formed thereon. In this example, the 4 mm×4 mm biosensors 204 have four 0.2 mm fiducials 802 on diagonals except for a 1 mm×1 mm center region. These fiducials 802 enable one to monitor the position of the microplate 206 in relation to the optical subsystem 150. This is important so that the plate alignment subsystem 160 can be used to properly locate the microplate 206 if it is removed from and then reinserted back into the measurement chamber 110 (see FIG. 1). Alternatively, FIGS. 9A and 9B are diagrams illustrating an alternative design where the intrawell fiducials 802 shown in FIGS. 8A-8B are not used but instead winged fiducials 902 formed on the microplate 206 are used. For a more detailed discussion about how these and several other types of fiducials can be used to properly locate the microplate 206 in the measurement chamber 130, reference is made to the following documents:
- U.S. patent application Ser. No. 11/027,547 entitled "Spatially Scanned Optical Reader System and Method for Using Same"
- U.S. patent application Ser. No. 11/210,920 entitled "Optical Reader System and Method for Monitoring and Correcting Lateral and Angular Misalignments of Label Independent Biosensors".

The contents of these documents are incorporated by reference herein.

2.2 Biosensor's Base Plate 603.

In one embodiment, the microplate 206 has an optical base plate 603 made from a glass substrate 706 that is covered by a coating of a UV cured resin (e.g., acrylate-based formulation) in which the diffractive grating structures 704 are replicated (see FIGS. 7, 8B and 9B). On top of the UV cured resin layer, a waveguide 702 is deposited which is made of a high refractive index transparent dielectric such as an inorganic oxide (e.g., $Nb_2O_5$ or $Ta_2O_5$). The optical waveguide 702 can be deposited using standard sputtering techniques. And, there may or may not be an ion gun assist, although the preferred embodiment includes the ion gun assist. An additional thin layer of $SiO_2$ may also be deposited on top of the waveguide 702 to enhance the biological binding capacity of the top surface on the waveguide 702. Although any sufficiently flat and optically transparent substrate 706 can be used that is made out of either plastic or glass, in the preferred embodiment, the glass substrate 706 is Corning's code 1737 F or G aluminosilicate glass. The preferred glass substrate 706 is 117.3 mm×76.1 mm (L×W) and has a thickness of 0.7 mm. FIGS. 8B and 9B are two top views of a base plate 603 that has 384 biosensors 204 incorporated therein that look like the biosensors 204 shown in FIGS. 8A and 9B.

2.3 Upper (Holey) Plate 602/Base Plate 603 Assembly.

As shown in FIGS. 6A-6B, the preferred microplate 206 is made by connecting a top (holey) plate 602 which has the wells 610 defined therein to the optical base plate 603. In the preferred embodiment, the top (holey) plate 602 is obtained by injection molding of COC-Ticona Topas® TKX-0001. The preferred (holey) top plate 602 has 384 round wells 610 and each well 610 has the following dimensions: top diameter 3.40 mm+/−0.05; bottom diameter 2.80 mm+/−0.05; height 10.92 mm; and volume 82.6 µl. Moreover, the preferred top (holey) plate 602 complies with the following standards:
- ANSI/SBS 1-2004 Footprint dimensions
- ANSI/SBS 2-2004 Height dimensions (the overall height of the plate is 14.22 mm)
- ANSI/SBS 3-2004 Bottom outside flange dimensions
- ANSI/SBS 4-2004 Well positions Also, in the preferred embodiment, the optical base plate 603 is attached to the holey plate 602 by using an adhesive (e.g., UV cationic epoxy—Loctite® 3340). For a detailed description about the preferred microplate 206 and the preferred adhesive assembly method, reference is made to the following documents:
- U.S. Patent Application No. 2003/0031829 A1 entitled "Multiwell Plate having Transparent Well Bottoms and Method for Making the Multiwell Plate".
- U.S. Pat. No. 6,767,607 B2 entitled "Multiwell Plate having Transparent Well Bottoms".
- U.S. patent application Ser. No. 11/046,427 entitled "Multiwell Plate and Method for Making Multiwell Plate Using A Low Cytotoxicity Photocurable Adhesive".

The contents of these documents are incorporated by reference herein.

2.4 Biosensor's Surface Attachment Chemistry.

As shown in FIG. 7, the preferred biosensor 204 has an attachment surface 716 which is used to bind the biomolecule 710 (target 710). For example, the attachment surface 716 can be formed by using a tie layer to covalently bind a reactive polymer to the top of the waveguide 702. Once the target 710 is immobilized, then blocker molecules are used to eliminate any unreacted groups from the reactive polymer. The blocker molecules can also used to create a reference area on top of the biosensor 204 (see FIG. 10).

In the preferred embodiment, the tie layer can be made from aminopropylsilsesquioxane (APS) or gamma-aminopropylsilane (GAPS), where APS is deposited from a solution and GAPS is vapour deposited. The reactive polymer can be made from poly(ethylene-alt-maleic anhydride) ("EMA") or poly(methylvinylether-alt-maleic anhydride) ("MAMVE"). And, any compound that eliminates the unreacted groups from the top surface can be used as blockers such as ethaloamine and O,O'-bis(2-aminopropyl)polyethylene glycol 1900. This type of surface chemistry allows the binding of a wide range of targets 610 including but not limited to: small peptides, ligands to proteins, antibodies, enzymes, receptors and cells.

For a detailed description about surface attachment chemistry, reference is made to the following documents:

U.S. patent application Ser. No. 10/996,952 entitled "Polymer-Coated Substrates for Binding Biomolecules and Methods of Making and Using Thereof".

U.S. patent application Ser. No. 11/027,509 entitled "Method for Creating A Reference Region and a Sample Region on a Biosensor and the Resulting Biosensor".

The contents of these documents are incorporated by reference herein.

2.5 Biosensor's Signal/Reference Areas.

In the preferred microplate 206, each well 610/biosensor 204 has a referencing area that is locally created by reacting the attachment chemistry with blocker molecules. The reference area is desired for several reasons. First, it allows the removal of effects from environmental changes such as temperature, background changes (e.g., differences in the index of refraction of the buffers), and repositioning changes caused by the removal and re-insertion of the microplate 206 into the optical reader 150. Second, it also allows the referencing of the non-specific binding of test compounds.

Figure 10:
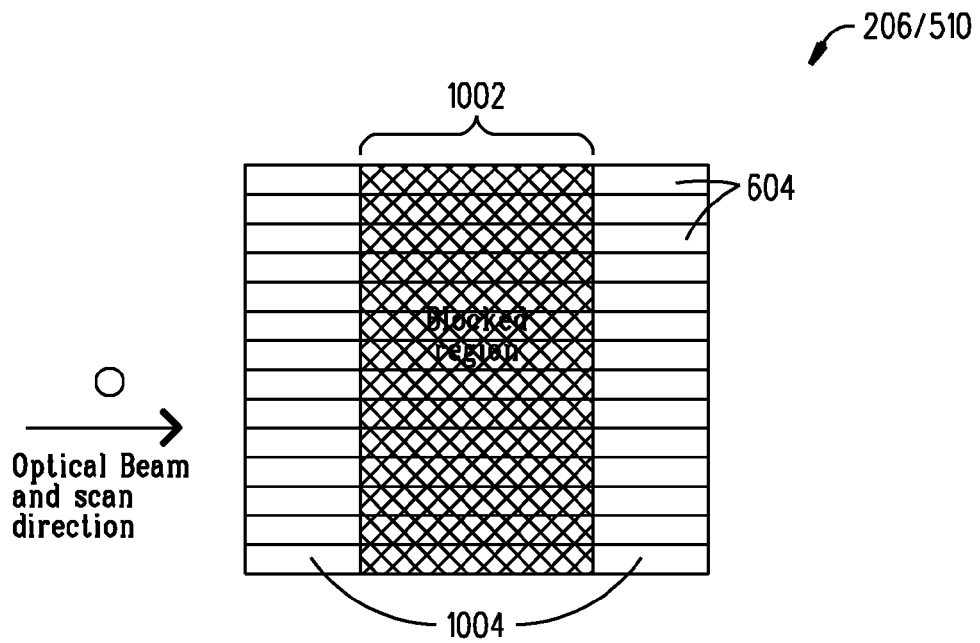
FIG. 10 is a top view of a biosensor that has two reference areas and one active area formed thereon by using surface active chemistry in accordance with one embodiment of the present invention.

In the preferred embodiment, the referencing area is created by patterning the bottom of the well 610 with the blocker material. There are several possible contact or non-contact methods for patterning a well 610, for instance, one contact method is to pinprint the blocker material in the well 610. In addition, each well 610 can have any one of a number of different reference area pattern(s) such as: 1) left/right half blocked; 2) center of diffraction grating blocked; and 3) alternating stripes or squares of blocked areas. In either case, the patterning of the wells 610 should be arranged along the axis of the diffraction gratings 704 as shown in FIG. 10 to avoid crosstalk between the reference region 1002 and the active regions 1004.

For a detailed discussion about the creation and use of a reference region 1002, reference is made to the aforementioned U.S. patent application Ser. No. 11/027,509. In addition, the following document describes several other types of self-referencing biosensors 204 that could be implemented in the present invention:

U.S. patent application Ser. No. 10/947,021 entitled "Self-Referencing Waveguide Grating Sensors".

The contents of this document are incorporated by reference herein.

A description is provided next about how the screening systems 100a, 100b and 100c can be used to perform different types of measurement assays. However, prior to discussing several exemplary measurement assays a brief discussion is provided about the functionality of the main components in the screening system 100. Referring again to FIGS. 1A-1C, block diagrams are shown which illustrate the different configurations of the screening systems 100a, 100b and 100c. As shown, the incubation chamber 110 (athermalization buffer 110) which has an environmentally controlled interior provides a buffer for a large number of microplates 206 to reach thermal equilibrium. This allows microplates 206 to come from outside the screening system 100 at an uncontrolled temperature and then equilibrate. The incubation chamber 110 is preferably large enough to allow multiple microplates 206 to come to equilibrium without limiting the throughput of the screening system 100. The load lock chamber 120 (only shown in FIG. 1A includes a rotating arm 135 (interface device 135), a multi-rail system 120b and a bar code reader 120c) is a transfer area between the incubation chamber 110 and the measurement chamber 130. The load lock chamber 120 is basically a vestibule through which the microplate 206 passes to get to the measurement chamber 130. The measurement chamber 130 which is also thermally controlled is where the optical interrogation of the microplate 206 occurs. The measurement chamber 130 includes: (1) a measurement module 150; (2) a liquid handling module (pipettor) 180a; (3) environmental control equipment 170; and (4) a microplate handling module (gripper or rails) 180b.

The screening systems 100a, 100b and 100c function to optically interrogate the biosensors 204 located on the bottoms of the wells 610 in a microplate 206. In the preferred configuration, the screening systems 100a, 100b and 100c use a column of optical beams 202 to scan a row of wells 610/biosensors 204 in a moving microplate 206 (see FIG. 2). In one embodiment, the optical interrogation beams 202 are scanned across the moving wells 610/biosensors 204, and the readings from both the active and blocked areas of the wells 610/biosensors 204 are detected and recorded. Alternatively, it is possible to move the optic head 222 so that the optical interrogation beams 202 are scanned across static wells 610/biosensors 204. To detect a binding event, a first scan needs to be taken after the target 710 is immobilized on the wells 610/biosensors 204. And, a second scan needs to be taken after a biological material 708 (analyte 708) has been introduced to the immobilized target 710 on the wells 610/biosensors 204. If necessary, the microplate 206 may be repositioned in the measurement chamber 130 by using the fiducials 802 (see FIGS. 8 and 9) before the second scan is obtained. Following is a detailed description about how the screening systems 100a, 100b and 100c can be used to perform two different types of measurement assays:

3.1 Assay mode.
3.2 HTS mode.

3.1 Assay Mode

Figure 11A:
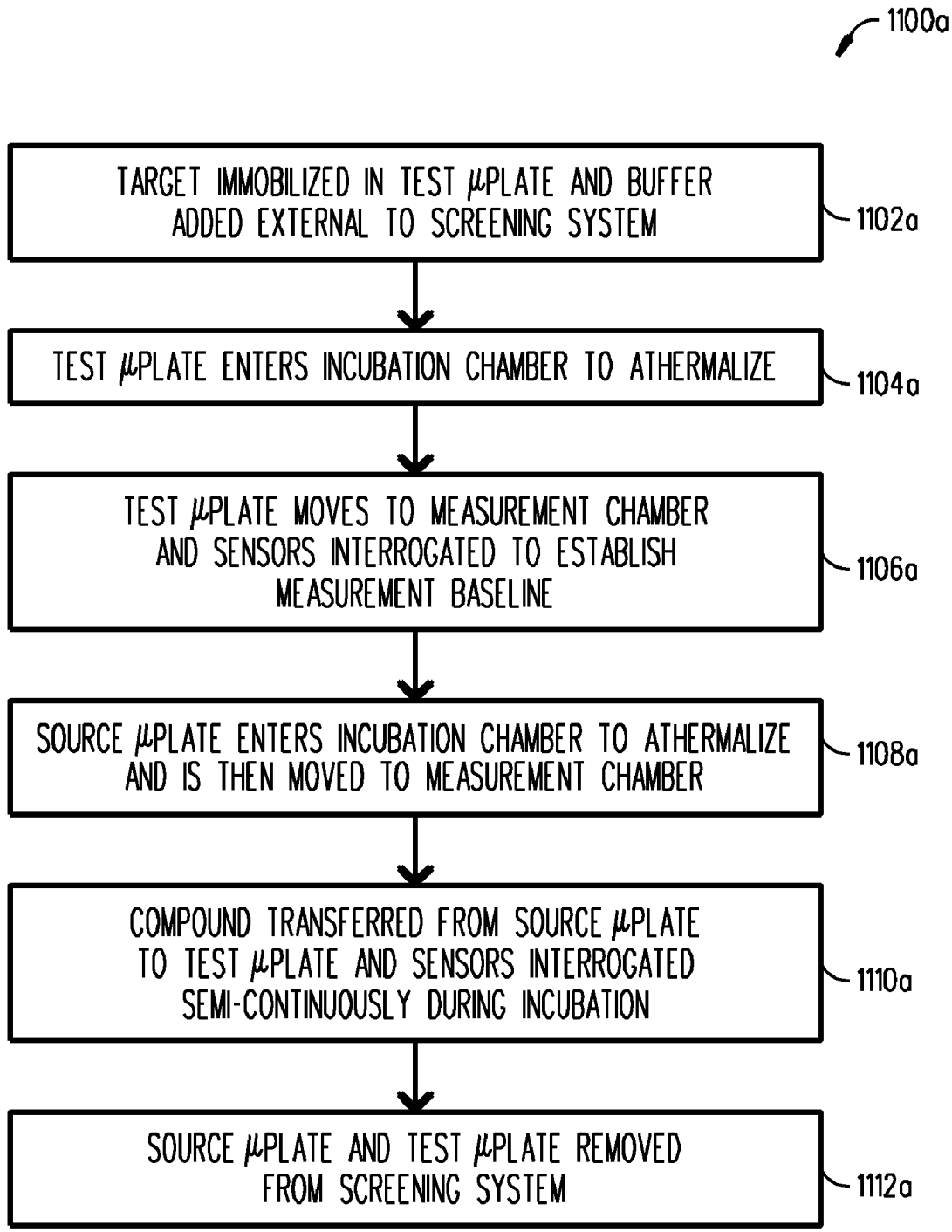
FIGS. 11A-11C are two flowcharts and a graph that are used to help explain different assays that can be performed by anyone of the screening systems shown in FIG. 1 while it is in an assay development mode in accordance with one embodiment of the present invention.
Figure 11B:
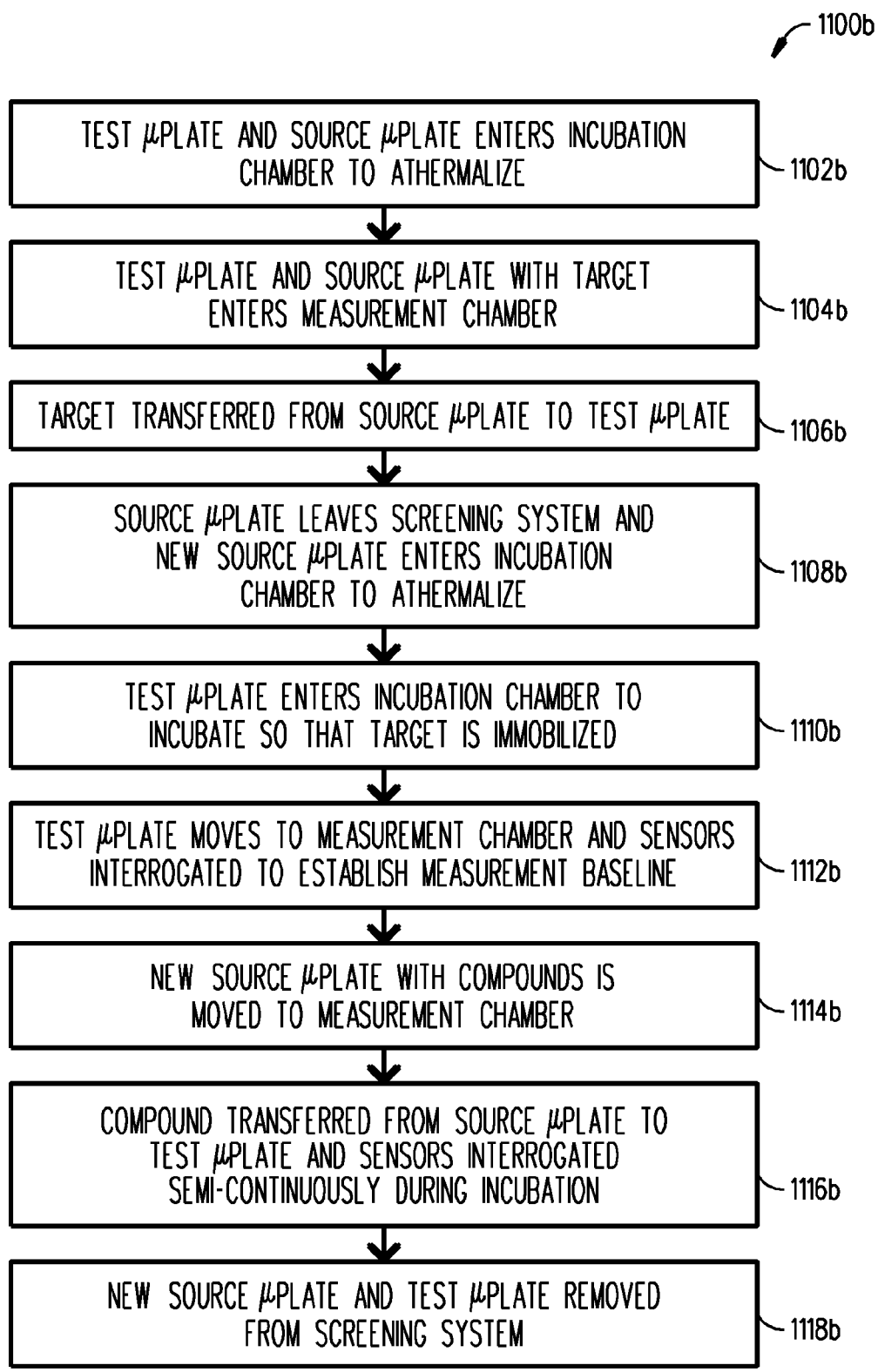

The screening systems 100a, 100b and 100c while functioning in the assay mode obtains in real time bio-chemical interaction data. FIGS. 11A and 11B are two flowcharts that are used to help describe two different types of assay modes which can be performed by the screening systems 100a, 100b and 100c. In the description below, a source microplate stores materials that are going to be transferred to a test microplate 206. And, the test microplate 206 has the biosensors 204 embedded in the bottom of the wells 610.

FIG. 11A is a flowchart that shows the steps of one serial method 1100a that can be performed by screening system 100a (for example) while it is in an assay development mode. Beginning at step 1102a, a therapeutic target 710 is immobilized inside the wells 610 of the test microplate 206 while it is located outside of the screening system 100. After the target 710 is immobilized, a buffer is added to the wells 610 in the microplate 206. At step 1104a, the test microplate 206 is inserted into the incubation chamber 110 so it can athermalize. It can take 30 minutes for the test microplate 206 to reach thermal equilibrium depending on ambient temperature of the test microplate 206. At step 1106a, the test microplate 206 is moved from the incubation chamber 110 to a measurement position in the measurement chamber 130 via the load lock chamber 120. While in the measurement chamber 130, the biosensors 204 in the test microplate 206 are interrogated to obtain a measurement baseline. Then at step 1108a, a source microplate is inserted into the incubation chamber 110 so it can athermalize. It should be noted that the source microplate can be inserted into the incubation chamber 110 at the same time the test microplate 206 was inserted into the incubation chamber 110. After a period of time, the source microplate is moved from the incubation chamber 110 to the measurement chamber 130 via the load lock chamber 120. At step 1110a, the liquid handling module (pipettor) 180a in the measurement chamber 130 transfers an analyte 708 (test compound 708) from wells in the source microplate to the wells 610 in the test microplate 206. And, then the biosensors 204 in the test microplate 206 are interrogated to obtain many different measurements during the incubation of the test microplate 206. Once the test microplate 206 has been interrogated, the test microplate 206 and the source microplate at step 1112a are both removed from the screening system 100. These steps can be repeated over and over to serially interrogate any number of test microplates 206. As can be seen, there are no throughput requirements in this mode, and hence there is no need to multiplex the test microplates 206 into and out of the screening system 100 like in the HTS mode (see FIGS. 12-15). Again, it should be appreciated that screening systems 100b and 100c do not have a load-lock chamber 120 and that screening system 100c has a measurement chamber 130 which contains the athermalization buffer 110. However, these screening systems 100b and 100c can perform the same type of assay as described above.

FIG. 11B is a flowchart that shows the steps of another type of serial method 1100b that can be performed by screening system 100a (for example) while it is in an assay development mode. Beginning at step 1102b, the test microplate 206 (which does not have a target 710 immobilized thereon) and a first source microplate (which contains a target 710) are inserted into the incubation chamber 110 so they can athermalize. It can take 30 minutes for the microplates 206 to reach thermal equilibrium depending on ambient temperatures of the microplates 206. At step 1104b, the test microplate 206 and the first source microplate are moved from the incubation chamber 110 to the measurement chamber 130 via the load lock chamber 120. At step 1106b, the liquid handling module (pipettor) 180a transfers the therapeutic target 710 from the wells in the first source microplate to the wells 610 in the test microplate 206. At step 1108b, the first source microplate is removed from the screening system 100 and a second source microplate is inserted into the incubation chamber 110 so it can athermalize. At step 1110b, the test microplate 206 is moved from the measurement chamber 130 to the incubation chamber 110 via the load lock chamber 120 so that the therapeutic target 710 can incubate and become immobilized inside the wells 610 of the test microplate 206. Then at step 1112b, the test microplate 206 is moved from the incubation chamber 110 to a measurement position in the measurement chamber 130 via the load lock chamber 120. At this point, the unbound target 710 is removed from the wells 610 in the microplate 204 and a buffer is added therein. Then, the biosensors 204 inside the test microplate 206 are interrogated to obtain a measurement baseline. Then at step 1114b, the second source microplate is moved from the incubation chamber 110 to the measurement chamber 130 via the load lock chamber 120. At step 1116b, the liquid handling module (pipettor) 180a transfers the test compound 708 from the wells in the second source microplate to the wells 610 in the test microplate 206. And, then the biosensors 204 in the test microplate 206 are interrogated to obtain many different measurements during the incubation of the test microplate 206. Once the test microplate 206 has been interrogated, the test microplate 206 and the second source microplate at step 1118a are both removed from the screening system 100. These steps can be repeated over and over to serially interrogate any number of test microplates 206. As can be seen, there are no throughput requirements in this mode, and hence there is no need to multiplex the test microplates 206 into and out of the screening system 100 like in the HTS mode (see FIGS. 12-15). Again, it should be appreciated that screening systems 100b and 100c do not have a load-lock chamber 120 and that screening system 100c has a measurement chamber 130 which contains the athermalization buffer 110. However, these screening systems 100b and 100c can perform the same type of assay as described above.

A more detailed description is provided next about how one can add the target 710 to the test microplate 206 and about how one can run the binding assay.

3.1a Adding Target 710:

The source microplate is first transferred to the source plate position in the measurement chamber 130 via the automated internal plate handling module 180a and 180b (see step 1104b). The test microplate 206 is also loaded in a measurement position in the measurement chamber 130. The source plate is then moved so it is located under the pipettor, the pipettor moves down to the source microplate and liquid is drawn up into the pipettor tips. Next, the test microplate 206 is moved so it is located under the pippettor, the pippettor moves down to the test microplate 206 and the fluid is transferred from the pipettor tips to the test microplate 206. The fluid handling devices 180a and 180b in the measurement system 130 also have the capability to mix the added fluid to the fluid already in the wells 610 of the test microplate 206 by drawing some amount the fluid volume back up into the pipettor tips and then re-depositing it into the wells 610 of the microplate 206. The mixing time can occur for as long as needed. The test microplate 206 is returned to the incubation chamber 110 to incubate (usually 30-90 minutes). After the target 710 has bound to the surface of the biosensors 204, the test microplate 206 moves under the pipettor, the pippettor moves down to the test microplate 206 and removes the remaining fluid with unbound target 710. Then, an index matched buffer is added to the wells 610 to dilute the remaining liquid in the wells 610. This is then removed. The aforementioned process is repeated until there is no free target 710 and only bound target 710 left in the wells 610 of the test microplate 206.

3.1b Running the Binding Assay.

A source microplate filled with a test compound(s) 708 is moved from the incubation chamber 110 to the source plate position in the measurement chamber 130 (see step 1114b). The test microplate 206 with the target 710 bound to the surface is moved to the test microplate position in the measurement chamber 130 (see step 1112b). The source microplate is moved under the pippettor tips and the pippettor tips move down to the source microplate so that the pipettor tips can be filled with the test compound(s) 708. Then, the test microplate 206 is moved to the measurement position. A baseline scan of the wells 610 with target 710 bound to the surface is taken (see step 1112b). After this, the pipettor is moved over the test microplate 206 and the test compounds 708 are added to the test microplate 206. The contents are mixed for some user controlled amount of time. The test microplate 206 which is located in the measurement position is then scanned (see step 1116b). After the scan, the contents of the wells 610 can again be mixed that the reaction is not diffusion limited. The mixing involves the drawing up of fluid into the pipettor tips and the squirting of the fluid back into the wells 610. The typical mixing time is about 6 minutes at the beginning of each assay. The binding signals as a function of time are obtained until the assay reaches completion. This time can range from 20 to 60 minutes, depending on the assay properties. This will limit the throughput rate of 384 well test microplates 206 to about 3000-10000 wells in an 8 hour period. However, this is not a problem since there are no set throughput requirements for the assay development mode.

Figure 11C:
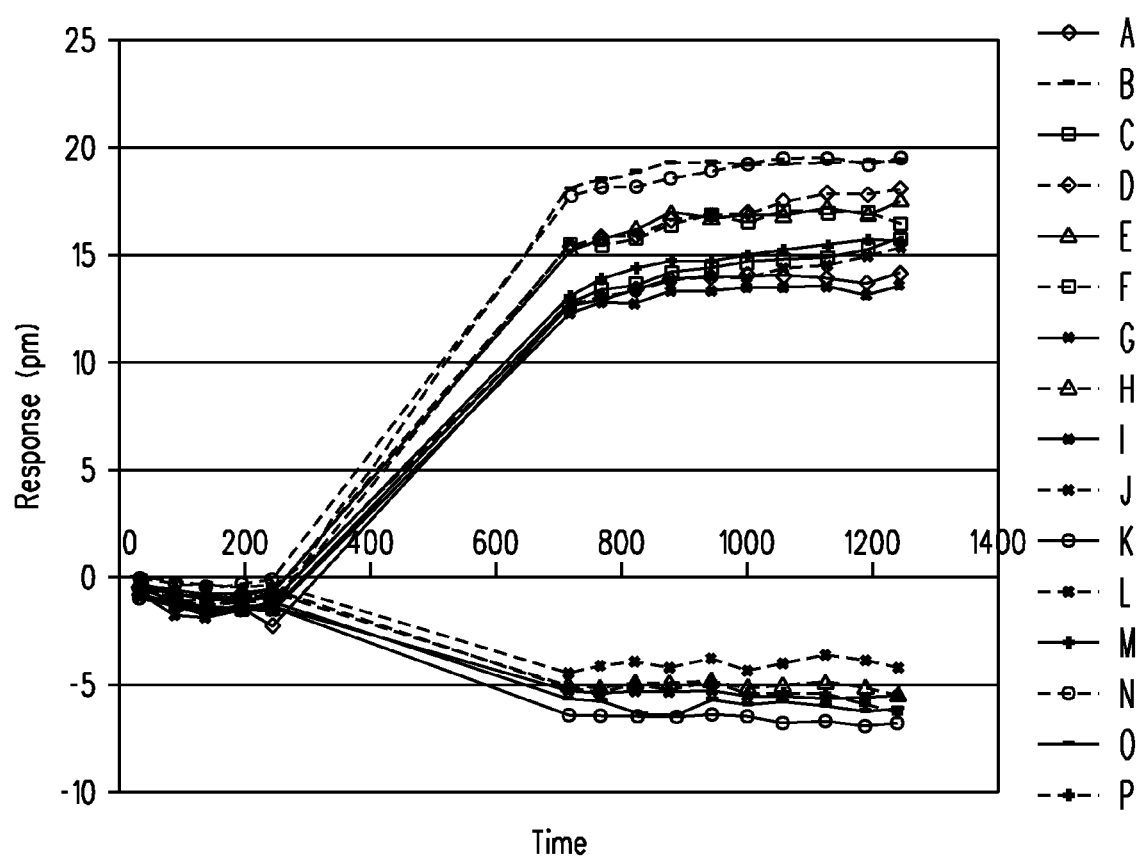

An example of the data obtained from this type of assay development operation is shown in FIG. 11C. The graph shows the responses from several wells 610 (wells A, B . . . P) as a function of time that were obtained simultaneously. The total binding was obtained by choosing an endpoint in the saturation region of the response (e.g. at 1000 seconds) and then taking the difference between wells 610 that had analyte 708 therein and the negative control wells 610 which were wells G, H, L, O, and P.

3.1 HTS Mode.

The screening system 100 includes several components and features that together allow direct-binding, label-free assays to be executed in a high throughput capacity. In the HTS mode, it is important to realize that the microplates 206 in which the label-free, direct-bind assay are being executed cannot be left in the screening system 100 for the entire duration of the assay. Because, if the duration of a typical label-free, direct-bind assay (including compound addition, but not target immobilization) is 20 minutes, then the maximum possible rate is only ~9,200 wells/8 hrs if the 384 well microplates 206 remain inside the screening system 100. This is well below the target rate of 40,000 wells/8 hrs which is defined herein as being high throughput. The screening system 100 can meet the 40,000 wells/8 hrs HTS goal by combining the end-point assays with the movement of 384 well microplates 206 into and out of the screening system 100.

Figure 12:
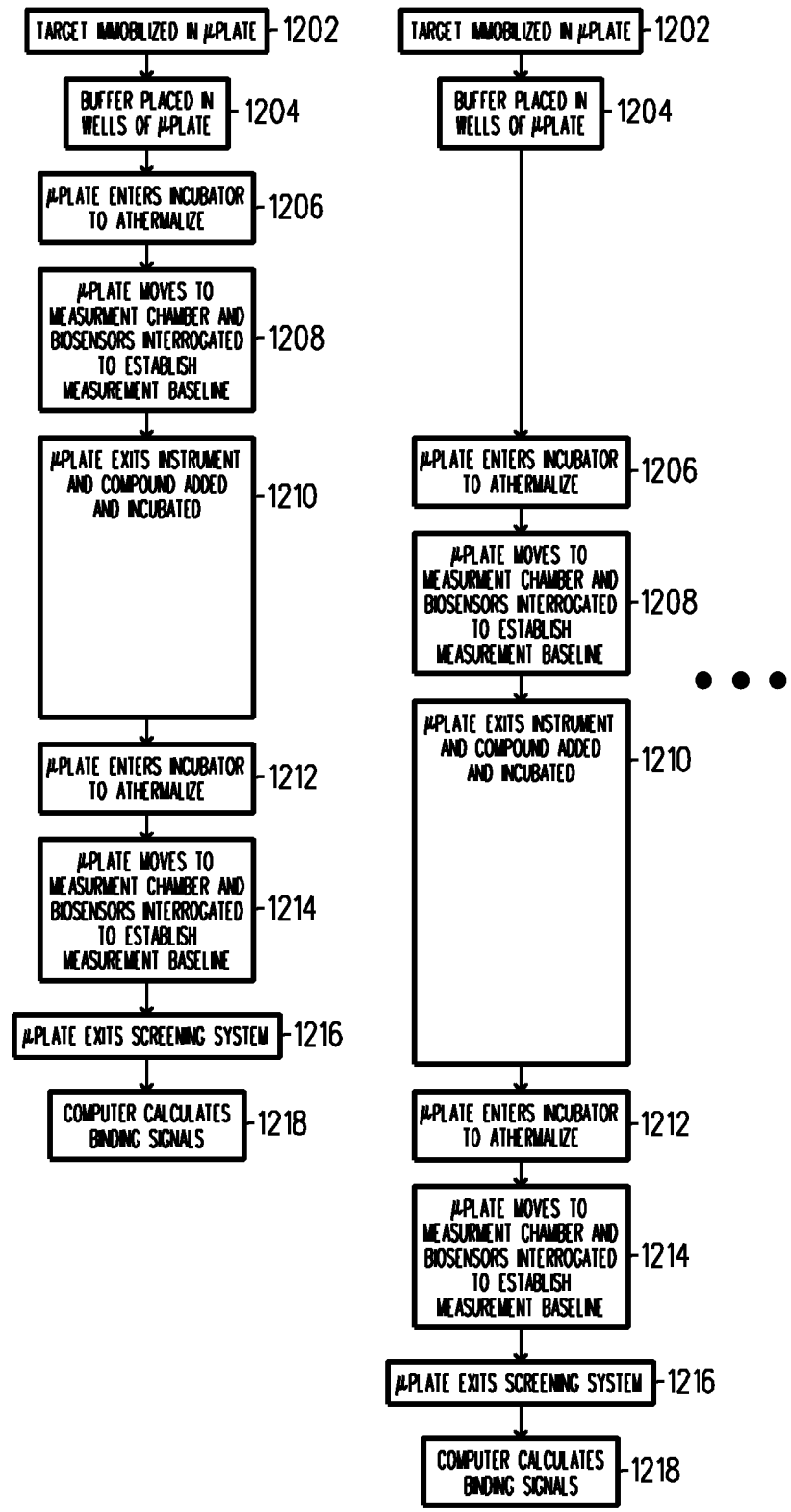
FIGS. 12-15 are different diagrams that are used to help explain a HTS assay that can be performed by anyone of the screening systems shown in FIGS. 1A-1C while it is in a HTS mode in accordance with another embodiment of the present invention.

FIG. 12 is a flowchart illustrating the steps of a HTS method 1000 that can be implemented by using the screening system 100a (for example) of the present invention. First, a 384 well microplate 206 has the target 710 attached to the surface of the biosensors 204 and the wells 610 are filled with a buffer whose index of refraction is matched to the index of the analyte's buffer (steps 1202 and 1204). In the preferred embodiment, steps 1202 and 1204 are performed outside of the screening system 100a. The microplate 206 is then placed in the incubation chamber 110 so it can reach a thermal equilibrium which usually takes about 30 minutes, but the time depends on ambient external temperature (step 1206). Then, the microplate 206 is transferred from the incubation chamber 110 to the measurement chamber 130 via the load lock chamber 120 (step 1208). In the preferred embodiment, the microplate 206 is removed from the incubation chamber 110 by a rotating arm associated with the load lock chamber 120 and transferred to one of the plate carriages in the load lock chamber 120 via a gripper. The plate carriage then moves the microplate 206 to the measurement chamber 130, which is kept to within 0.1° C. of the incubation chamber 110. It should be appreciated that the measurement chamber 130 may also have several athermalization positions therein in which microplates 206 can be placed to further athermalize. This would be needed if the incubation chamber 110 does not have the same thermal profile as the measurement chamber 130. After all of this, another gripper then inserts the microplate 206 into the measurement nest 400, and a baseline measurement of the microplate 206 is obtained in about 240 seconds by moving the microplate 206 across the optical reader 140 (step 1208). After the baseline scan of the microplate 206 is obtained, the microplate 206 is removed from the measurement position and loaded onto a second carriage. The rotating arm then transfers the microplate 206 to external equipment (e.g., see FIG. 13) which adds the analyte 708 to the wells 610 in the microplate 206 (step 1210). At this point, the microplate 206 can either be returned to the incubation chamber 110 to incubate, or it can be incubated in the external equipment (step 1210). It usually takes about 30 minutes for direct bind assays to incubate. After which, the microplate 206 is returned to the incubation chamber 110 so it can once again reach a thermal equilibrium (step 1212). Then, the microplate 206 is transferred back to the measurement chamber 130 via the load lock chamber 120 and interrogated once again (step 1214). Again, it can take about 240 seconds to scan the microplate 206. Thereafter, the microplate 206 is removed from the screening system 100 (step 1216). The computer 140 then calculates the binding signal from the difference of the two readings (see step 1218). The computer 140 can also utilize intrawell referencing as necessary to remove system wavelength shifts not related to the binding of the analyte 708 to the target 710. As shown in FIG. 12, this process can be repeated multiple times by multiplexing microplates 206 into and out of the screening system 100 in order to meet the desired HTS requirement. Again, it should be appreciated that screening systems 100b and 100c do not have a load-lock chamber 120 and that screening system 100c has a measurement chamber 130 which contains the athermalization buffer 110. However, these screening systems 100b and 100c can perform the same type of HTS assay as described above.

To also help meet the desired HTS requirement, the screening system 100 can have several positions (park positions) that microplates 206 can be placed which puts them in the queue for the next step or measurement without requiring the full time it takes to move from the incubation chamber 110 to the measurement chamber 130. For instance, there can be one park position near the rotating arm in the load lock chamber 120 to handle microplates 206 coming into and going out of the screening system 100, and there can be another park position in the form of an additional carriage for moving the microplates 206 into and out of the measurement chamber 130.

As can be seen, to implement this HTS protocol, specific functions should be integrated into the screening system 100. These functions are:

A plate handling system for moving the microplate 206 into and out of the screening system 100.
 A plate-handling/data-point read cycle that has a duration that is shorter than the minimum required/allowed assay duration.
 A plate ID and data processing solution that allows endpoint assay data to be tracked and calculated.
 A system implementation of the above three that allows plate multiplexing to achieve the target rate for the HTS.

Furthermore, the screening system 100 has additional components which are used to help execute the above described HTS protocol:

Microplate 206/sensors 204 with intra-well referencing to reference out any residual optical/mechanical alignment errors, sensor material drift, and environmental/thermodynamic induced drift.
 Optical/mechanical platform 400 that is insensitive to minor alignment perturbations due to plate in/out.
 Optical reader 150 and microplate subsystem design that allows both reference and signal regions of the biosensors 204 to be interrogated.

It should be noted that the screening system 100 described above is just one specific embodiment that can be used to execute these functions to enable the aforementioned HTS protocol. It should also be noted that this HTS protocol is not limited to just microplate based label-free assays, but it can be applied to other non-microplate based platforms as well (microarrays, etc.).

As mentioned above, the screening systems 100a, 100b and 100c may need to interact with external equipment like a high throughput screening (HTS) line to help implement this HTS protocol. A block diagram is provided in FIG. 13 that illustrates one example of how the screening system 100 with the aid of a rotating arm 1302 can interact with an exemplary HTS line 1304. The exemplary HTS line 1304 includes a robot arm 1306a, a fluorescence reader 1306b, a stacker/hotel 1306c, a pipettor 1306d, an incubator 1306e (two shown) and a gripper pipettor 1306f (for example).

Figure 14:
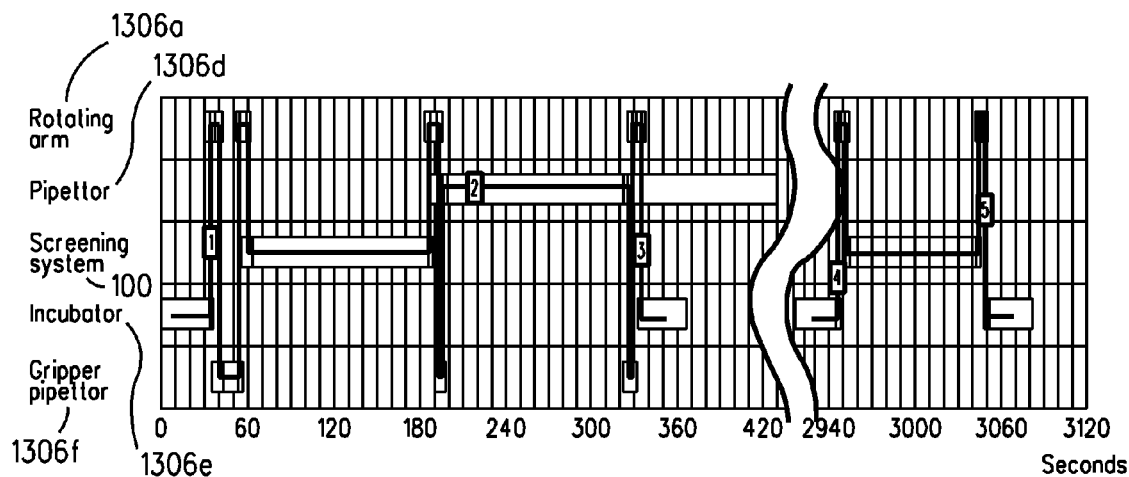

FIG. 14 is a gantt chart that illustrates one way the screening system 100a (for example) can interact with the HTS line 1304 to implement the HTS protocol (see FIGS. 12 and 13). The chart illustrates the location of a single microplate 206 in the screening system 100a and in the HTS line 1304 at different times during the assay. Again, the rotating arm 1302 is the interface between the screening system 100 and the HTS line 1304.

Figure 15:
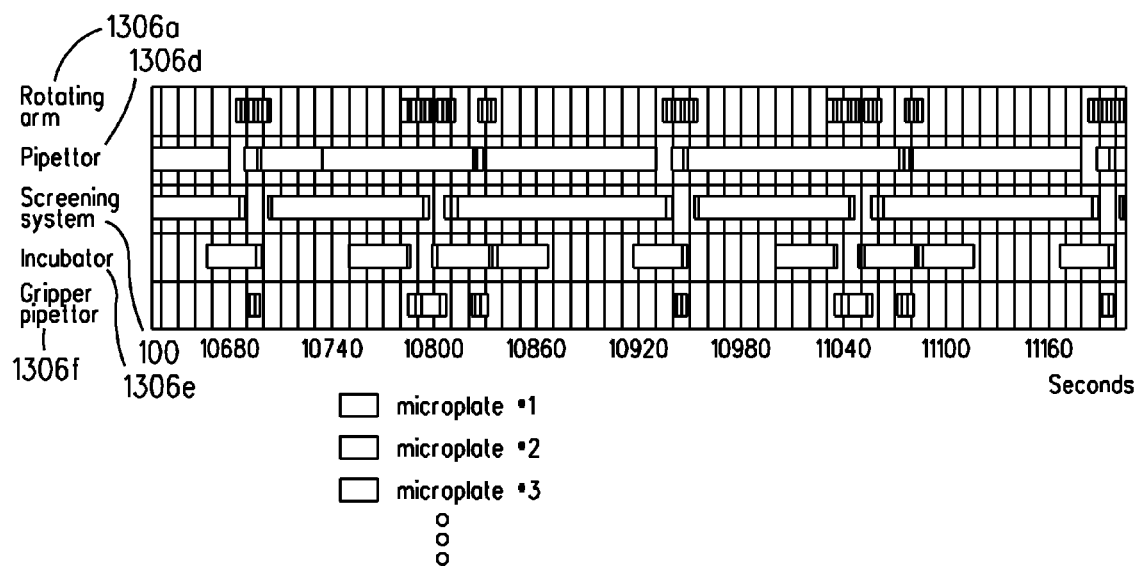

FIG. 15 is a chart that is used to illustrate how the screening system 100a (for example) can be operated in steady state to obtain a scanned rate of 40,000 wells/8 hrs. The chart shows how several 384 well microplates 206 can be in different stations to most efficiently interleave them and to maximize the utilization of each piece of equipment in the screening system 100a and the HTS line 1304. It should be noted that there are many different forms and types of HTS lines that can be interfaced with the screening system 100a.

Figure 16:
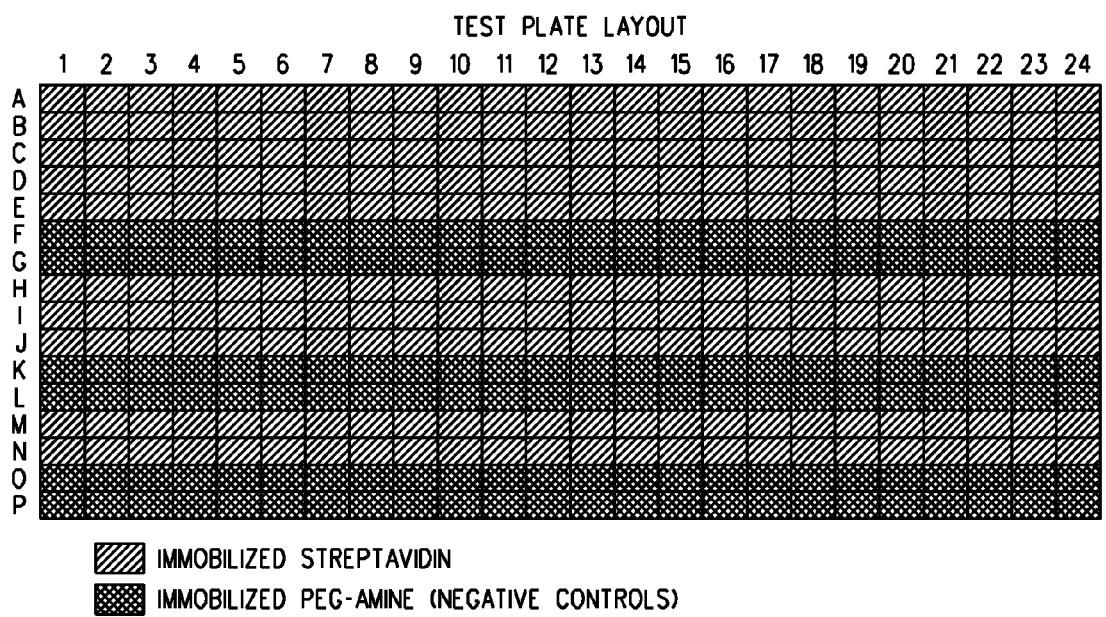
FIGS. 16-17 are two diagrams used to help describe a particular assay protocol and it's results using the screening system of the present invention.

A description is provided next about an exemplary protocol that was implemented by the screening system 100 to perform an assay that consisted of binding fluorescein biotin (831 Da) 708 to protein streptavidin (60 kDa) 710 which was immobilized at the bottom of selected wells 610 in a 384-well microplate 206. Although this protocol was designed for a full plate assay, any number of columns could be run to suit individual needs. This assay used interwell referencing for calculating the wavelength shift resulting from binding events. The steps used to perform the assay were as follows:

A. Test Plate Preparation (See FIG. 16)
1) Add 15 µl of 50 µg/mL streptavidin in 20 mM acetate buffer, pH 5.5 into wells A-F, I, J, M, N of the microplate 206.
2) Add 15 µl of 20 mg/mL PEG-amine in 100 mM borate buffer, pH 9 into wells G, H, K, L, O, & P. These wells were used as negative controls.
3) Mix the solutions by aspiration and dispensing the solution repeatedly, incubate 20 minutes at room temperature, then mix again.
4) Remove the solutions from all wells and rinse with buffer repeatedly.
5) Add 20 µl of 200 mM ethanolamine in 150 mM borate buffer, pH 9.2 to all wells and mix. Remove and discard the solutions from all wells.
6) Add 20 µl of 200 mM ethanolamine in 150 mM borate buffer, pH 9.2 to all wells and mix. Incubate for 5 minutes, mix and rinse with buffer repeatedly.
7) Allow the plate to soak in PBS buffer for 4 hours prior to running the binding assay.

B. Source Plate Preparation
1) Add 250 µl of 200 nM fluorescein biotin in 1×PBS to each well of a V-bottom 96-well microplate.
2) Cover the microplate with aluminum seal or a plastic lid to avoid evaporation; the cover was removed 30 minutes prior to performing the binding assay (see note 1 below).

C. Instrument Assay Recipe
Note 1: For optimal performance, the source and test plates should be docked in the screening system 100 and allowed to sit, uncovered, for 30 minutes to achieve thermal equilibrium prior to running the assay.
Note 2: Test plate is pre-filled with 15 µl of 1×PBS prior to docking the plate in the screening system 100.
1) Take a baseline measurement of the microplate 206.
2) Add 15 ul of 200 nM fluorescein biotin.
3) Mix the solutions in the wells 610 by aspiration and dispensing
4) Measure the optical signal.

Figure 17:
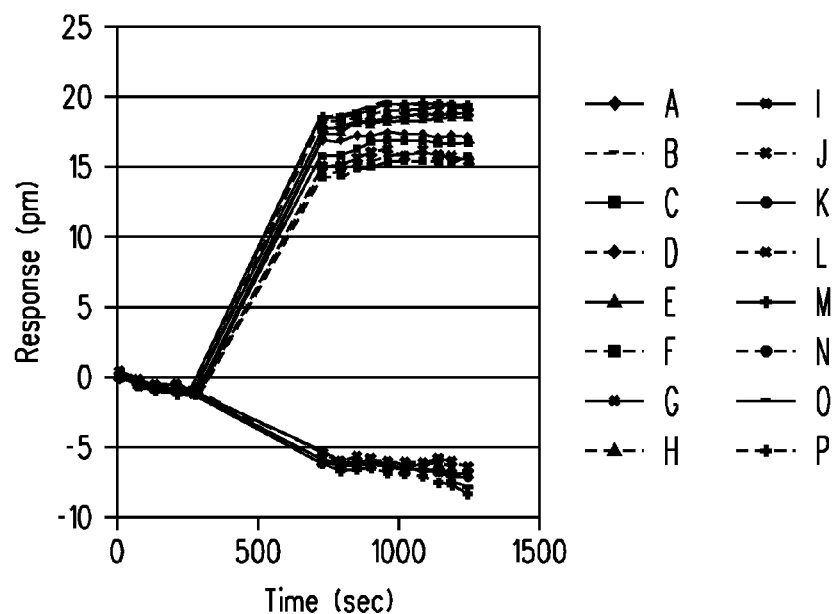

D. Assay Results/Data Analysis
The shift in wavelength for each well 610 was calculated by taking the difference in response between an initial reading (at 200 sec) and a final reading (at 1200 sec). The data was then referenced (to correct for drift, bulk index of refraction effects, etc) by subtracting the average shift in wavelength for the control wells in each column, from each well in the column. FIG. 17 is a graph illustrating the results of the assay.

E. Conclusion
The screening system 100 operating in assay development mode running the above protocol for 13 plates provided a coefficient of variance of 7.9% over 3091 active wells, and 1872 reference wells. There were 59 wells rejected as outliers due values greater than 3 sigma from the mean response.

Following are some advantages, features and uses of the present invention:

1. The screening systems 100a, 100b and 100c can be used in more types of assays then HTS screening. It can be employed in any application where detection of biological binding is necessary. These other applications include but are not limited to diagnostics, food safety, and homeland security.

2. Label free detection compared to radioactive and fluorescence detection: HTS detection technologies in the prior art use either labels or color inducing compounds in a biochemical enzymatic reaction such as the ones used in ELISA (enzyme linked immunosorbent assays). Fluorescent labels as well as labelling strategies have been developed that allow the detection of the interaction of a drug compound with a therapeutic target in HTS using either fluorescence intensity, fluorescence polarization, fluorescent resonant energy transfer including time resolved techniques. A review on these techniques was published (see A. J. Pope, et al. 'Homogeneous fluorescence readouts for miniaturized HTS: theory and practice', Drug Discovery Today, 4, 1999, 350). It is well known that the labels can be a source of artifacts that affect the reliability of the screening results. And, comparisons between labelling and detection strategies used in HTS showed significant differences in the number and nature of the identified 'active' compounds (e.g., M. A. Sills et al. 'Comparison of Assay Technologies for a Tyrosine Kinase Assay Generates Different Results in HTS', J. Biomolecular Screening, 7, 2002, 191). The label free detection method of the present invention also has an advantage over radioactive assays because there is none of the difficulty with respect to handling and disposal of the radioactive material.

3. Direct bind assays are possible: The use of labels usually prevents the detection of the direct interaction of a drug compound with the therapeutic target of interest because the labelling of the target may affect its biochemical activity. Assays for HTS are therefore designed as 'functional' assays in which a natural ligand or substrate (in the case of an enzyme) is labelled at least once and allowed to interact with the target hereby generating a negative or baseline signal. The interaction of the drug compound with the target or its ligand is detected via a change of this baseline signal. As can be seen, these functional assays for HTS are difficult to develop into robust and unambiguous screens. However, the label free HTS screening system 100 enables a simple assay in which the interaction of the compounds with the biomolecular therapeutic target alone is detected.

4. Sensitivity with low variability: The HTS screening system 100a, 100b and 100c are sensitive enough to detect direct interaction of compounds with large biomolecular targets immobilized on the surface of the biosensors in each well.

5. Intra-well referencing combined with plate in/out to allow end-point assays and plate multiplexing to achieve high throughput: HTS detection technologies and assay designs are usually based on end point readings during the detection step. The HTS screening systems 100a, 100b and 100c allows end point readings of 96 and 384 well microplates 206 including a base line reading prior to the incubation step in which compounds 708 are allowed to interact with the target 710 for a chosen amount of time without compromising the overall throughput.

6. Standard SBS format microplate compared to sensor chips: The HTS screening systems 100a, 100b and 100c uses SBS standard (ANSI/SBS 1 to 4-2004) sized microplates instead of specialty sensing chips. This is important since the specialty sensing chips have little or no compatibility with existing automated fluid handling and plate handling instrumentation.

7. Integration of standard fluid and plate handling units: The microplates and reader parts of the HTS screening system 100 can be integrated with a variety of fluid handling and plate handling instruments thereby increasing its modularity.

8. Assay development (real time) and HTS (end point) measurement modes possible on a single system: The screening systems 100a, 100b and 100c allows for a seamless operation between an assay development mode in which data can be acquired in real time (see FIGS. 11A-11C) and a HTS mode in which data can be acquired in two measurements (see FIGS. 12-15).

Although several embodiments of the present invention have been illustrated in the accompanying Drawings and described in the foregoing Detailed Description, it should be understood that the invention is not limited to the embodiments disclosed, but is capable of numerous rearrangements, modifications and substitutions without departing from the spirit of the invention as set forth and defined by the following claims.

What is claimed is:

1. A screening system comprising:
    a microplate;
    an interface device; and
    a measurement chamber into which the microplate is moved by the interface device, the measurement chamber having located therein at least the following:
        a plate transport subsystem which receives the microplate from the interface device;
        an optical subsystem;
        a plate alignment subsystem including a microplate mounting mechanism onto which the microplate is positioned by the plate transport subsystem so that biosensors located in wells of the microplate are interrogated by the optical subsystem, wherein the microplate has at least one angled fiducial marking located outside of the wells where the at least one angled fiducial marking is used to properly position/reposition the microplate relative to the optical interrogation subsystem;
        wherein the microplate mounting mechanism includes a base having at least one surface defining a nesting receptacle for the microplate, and at least three supports projecting from the base, the at least three supports support said microplate, said nesting receptacle has at least two side walls and at least two end walls, the nesting receptacle having walls further defining a detection aperture thereby allowing optical access to a bottom surface of the microplate through the detection aperture; and
        wherein the microplate mounting mechanism further includes at least two X-directional contacts located on one of the end walls and at least one Y-directional contact located on one of the side walls, and at least one spring-loaded contact on the end wall opposite the X-directional contacts and at least one spring-loaded contact on the side wall opposite the Y-directional contact.

2. The screening system of claim 1, further comprising a computer operatively connected to the interface device, the plate transport subsystem, the optical subsystem, and the plate alignment subsystem.

3. The screening system of claim 1, wherein said interface device includes:
    a rotating arm;
    a drawer;
    a lifter;
    a gripper;
    a carriage;
    a rail; or
    a conveyor.

4. The screening system of claim 1, wherein each biosensor is a resonant waveguide grating (RWG) biosensor.

5. The screening system of claim 1, wherein said plate transport subsystem includes:
    a rotating arm;
    a plate carriage;
    a gripper;
    a lifter; and/or
    a conveyor system.

6. The screening system of claim 1, wherein said plate alignment subsystem further includes an X-Y support stage.

7. The screening system of claim 1, further comprising a fluid handling subsystem which is located within the measurement chamber.

8. The screening system of claim 1, wherein the optical subsystem obtains a scanned rate of 40,000 wells in 8 hours.

9. The screening system of claim 1, wherein the optical subsystem scans a 384 well microplate in about 240 seconds.

10. The screening system of claim 1, wherein the measurement chamber further having located therein a measurement nest, an environmental control subsystem, and a fluid handling subsystem.

11. The screening system of claim 1, further comprising an athermalization buffer.

12. The screening system of claim 11, wherein the measurement chamber has located therein the athermalization buffer.

13. The screening system of claim 1, wherein the microplate mounting mechanism further includes one or more adjustment/s to position the microplate which include: one or more X-directional contact adjustment/s, one or more Y-directional contact adjustment/s, one or more spring-loaded adjustment/s, and/or at least one adjustment for the at least three supports.

14. A screening system comprising:
    a microplate;
    an interface device; and
    a measurement chamber into which the microplate is moved by the interface device, the measurement chamber having located therein at least the following:
        a plate transport subsystem which receives the microplate from the interface device;
        an optical subsystem;
        a plate alignment subsystem including a microplate mounting mechanism onto which the microplate is positioned by the plate transport subsystem so that biosensors located in wells of the microplate are interrogated by the optical subsystem, wherein the microplate mounting mechanism includes a base having at least one surface defining a nesting receptacle for the microplate, and three supports projecting from said base, said supports contact an underside surface of said microplate to support said microplate in a Z-directional plane, said nesting receptacle has at least two side walls and at least two end walls, said nesting receptacle further has two X-directional contacts and one Y-directional contact respectively located on one of said end walls and on one of said side walls, said nesting receptacle also has at least one spring-loaded contact on said end wall opposite said X-directional contacts and at least one spring-loaded contact on said side wall opposite said Y-directional contact, where the two X-directional contacts and the one Y-directional contact establish X-directional and Y-directional positions of a corner of said microplate.

* * * * *